(12) United States Patent
Talton et al.

(10) Patent No.: US 6,984,404 B1
(45) Date of Patent: Jan. 10, 2006

(54) METHODS FOR PREPARING COATED DRUG PARTICLES AND PHARMACEUTICAL FORMULATIONS THEREOF

(75) Inventors: James D. Talton, Gainesville, FL (US); Guenther Hochhaus, Gainesville, FL (US); Rajiv K. Singh, Gainesville, FL (US); James M. Fitz-Gerald, Schuyler, VA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/856,415

(22) PCT Filed: Nov. 18, 1999

(86) PCT No.: PCT/US99/27401

§ 371 (c)(1),
(2), (4) Date: Jul. 2, 2001

(87) PCT Pub. No.: WO00/28969

PCT Pub. Date: May 25, 2000

Related U.S. Application Data

(60) Provisional application No. 60/110,291, filed on Nov. 30, 1998, provisional application No. 60/108,847, filed on Nov. 18, 1998.

(51) Int. Cl.
*A61K 9/16* (2006.01)
*A61K 9/14* (2006.01)
*A61L 9/04* (2006.01)

(52) U.S. Cl. ............... 424/490; 424/493; 424/494; 424/497; 424/45; 424/46

(58) Field of Classification Search ............. 424/490, 424/493, 494, 447, 45, 46, 497
See application file for complete search history.

(56) References Cited

U.S. PATENT DOCUMENTS

| | | | |
|---|---|---|---|
| 4,046,712 A | 9/1977 | Cairns et al. | |
| 4,200,669 A | 4/1980 | Schaefer et al. | |
| 4,623,588 A | 11/1986 | Nuwayser et al. | |
| 4,656,056 A | 4/1987 | Leuenberger | |
| 4,678,772 A * | 7/1987 | Segal et al. ............ | 514/25 |
| 4,848,673 A | 7/1989 | Masuda et al. | |

(Continued)

FOREIGN PATENT DOCUMENTS

DE    3541999 A1    6/1987

(Continued)

OTHER PUBLICATIONS

Serafin Drugs used in the treatment of asthma Goodman and Gilman: The Pharmacological Basis of Therapeutics McGraw-Hill 9th ed CH 28 pp. 664-666 1996.*

(Continued)

*Primary Examiner*—Thurman K. Page
*Assistant Examiner*—Humera N. Sheikh
(74) *Attorney, Agent, or Firm*—Akerman Senterfitt

(57) ABSTRACT

Disclosed are methods using pulsed laser ablation to prepare coated drug particles of uniform size and thickness. The coated drug particles ranged in size from several nanometers to several millimeters in diameter size, and were coated with organic polymer particle having average diameter sizes from about 1 to 50 nm. In illustrative embodiments, coated drug particles or drug delivery particles are disclosed comprising a biodegradable or biocompatible polymer coating having controlled thickness and controlled coating uniformity, that offer superior pharmaceutical properties for controlled delivery and increased bioavailability.

36 Claims, 10 Drawing Sheets

U.S. PATENT DOCUMENTS

Figure 1A:
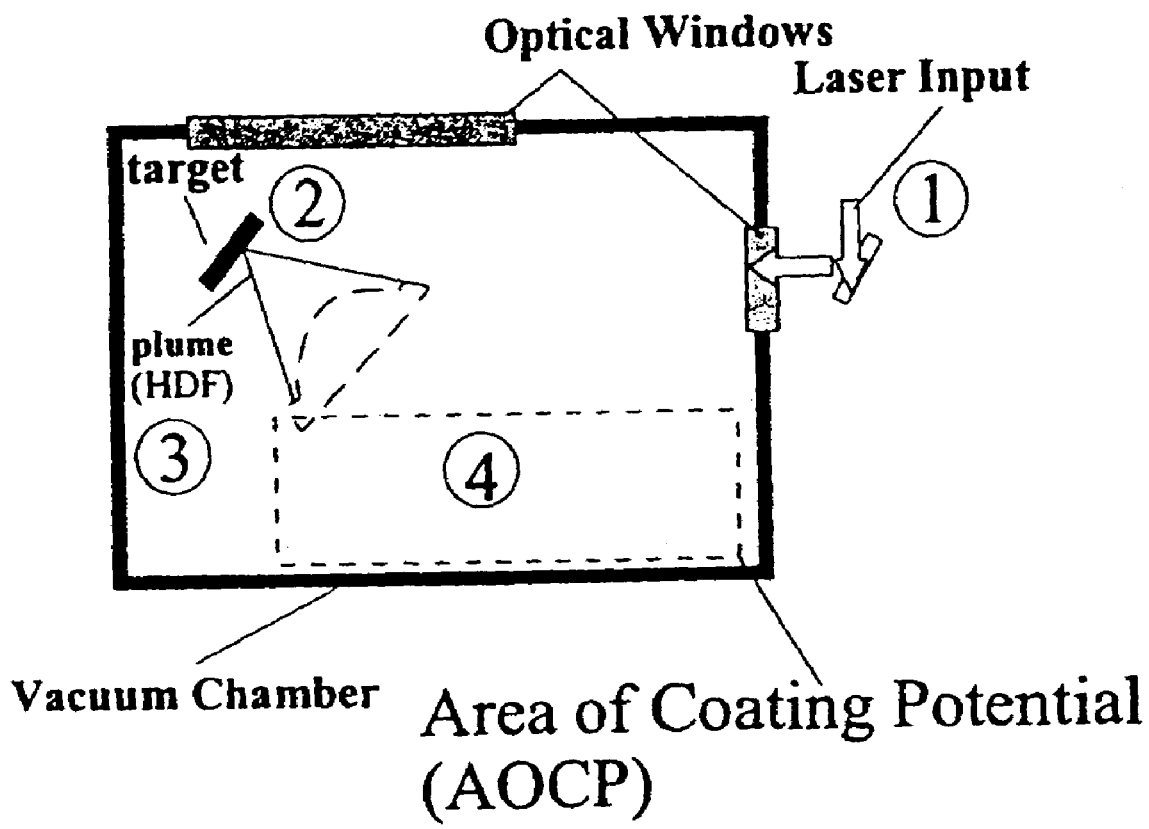

| | | | |
|---|---|---|---|
| 5,223,244 A * | 6/1993 | Moro et al. .................... | 424/45 |
| 5,242,706 A | 9/1993 | Cotell et al. | |
| 5,288,528 A | 2/1994 | Blanchet-Fincher | |
| 5,399,363 A | 3/1995 | Liversidge et al. | |
| 5,399,636 A | 3/1995 | Alt et al. | |
| 5,437,889 A | 8/1995 | Jones | |
| 5,456,917 A | 10/1995 | Wise et al. | |
| 5,466,468 A | 11/1995 | Schneider et al. | |
| 5,489,449 A | 2/1996 | Umeya et al. | |
| 5,499,599 A * | 3/1996 | Lowndes et al. | |
| 5,536,508 A | 7/1996 | Canal et al. | |
| 5,543,158 A | 8/1996 | Gref et al. | |
| 5,580,579 A | 12/1996 | Ruddy et al. | |
| 5,641,515 A | 6/1997 | Ramtoola | |
| 5,641,745 A | 6/1997 | Ramtoola | |
| 5,656,016 A | 8/1997 | Ogden | |
| 5,693,340 A | 12/1997 | Harth et al. | |
| 5,697,899 A | 12/1997 | Hillman et al. | |
| 5,702,716 A | 12/1997 | Dunn et al. | |
| 5,725,871 A | 3/1998 | Illum | |
| 5,756,353 A | 5/1998 | Debs | |
| 5,766,557 A | 6/1998 | Luy et al. | |
| 5,770,219 A | 6/1998 | Chiang et al. | |
| 5,779,708 A | 7/1998 | Wu | |
| 5,780,045 A | 7/1998 | McQuinn et al. | |
| 5,783,208 A | 7/1998 | Venkateshwaran et al. | |
| 5,792,451 A | 8/1998 | Sarubbi et al. | |
| 5,797,898 A | 8/1998 | Santini, Jr. et al. | |
| 5,804,212 A | 9/1998 | Illum | |
| 5,814,344 A | 9/1998 | Tice et al. | |
| 5,820,833 A | 10/1998 | Kawamura | |
| 5,849,265 A | 12/1998 | Li-Bovet et al. | |
| 5,855,913 A * | 1/1999 | Hanes et al. .................. | 424/43 |
| 5,922,306 A | 7/1999 | Akehurst et al. | |
| 5,972,388 A * | 10/1999 | Sakon et al. | |
| 5,976,577 A * | 11/1999 | Green et al. | |
| 6,001,336 A | 12/1999 | Gordon | |
| 6,025,036 A | 2/2000 | McGill et al. | |
| 6,074,135 A | 6/2000 | Tapphorn et al. | |
| 6,087,003 A | 7/2000 | Benoit et al. | |
| 6,129,905 A * | 10/2000 | Cutie .......................... | 222/402 |
| 6,277,364 B1 * | 8/2001 | Bucks et al. ................ | 424/401 |
| 6,406,745 B1 * | 6/2002 | Talton ....................... | 424/1.13 |

FOREIGN PATENT DOCUMENTS

| | | |
|---|---|---|
| DE | 42 39 244 A1 | 11/1992 |
| WO | WO 90/02546 | 3/1990 |
| WO | WO 98/53767 | 12/1998 |
| WO | WO 99/47726 | 9/1999 |
| WO | WO 00/28969 | 5/2000 |

OTHER PUBLICATIONS

Swinyard E.A. "Analgesics and Antipyretics" Remington's Pharmaceutical Sciences, 15th Edition, Chapters 59, 88 and 89, pp. 1035-1038 and 1570-1580.

Banker and Rhodes, Eds. Modern Pharmaceutics, Marcel Dekker, Inc. New York, 19990.

Hardy, et al. "Sustained Release Drug Delivery to the Lungs" Clin. Pharm. 2000 Jul.: 39(1): pp. 1-4.

Talton, et al. "Nano-Thin Coatings for Improved Lung Targeting of Glucocorticoid Dry Powders: In-Vitro and In-Vivo Characteristics" Respiratory Drug Deliver, VII, 2000, pp. 67-74.

Sato et al. "Porous Biodegradable Microspheres for Controlled Drug Delivery. 1. Assessment of Processing Conditions and Solvent Removal Techniques" Pharmaceutical Research, vol. 5, No. 1, 1988, pp. 21-30.

Thies, C "Microcapsules As Drug Delivery Devices" Critical Review in Biomedical Eng., vol. 8, Issue 4, pp. 335-383.

Bourlais, et al. "Ophthalmic Drug Delivery Systems — Recent Advances" Progress in Retinal and Eye Research, vol. 17, No. 1, 1998, pp. 33-58.

Talton, J.D. "Pulmonary Targeting of Inhaled Glucocorticoid Dry Powders" Thesis, university of Florida, 1999, pp. 1-135.

Hausberger, et al. "Characterization of Biodegradable Poly (D, L-lactide-co-glycolide) Polymers and Microspheres" Journal of Pharmaceutical & Biomedical Analysis, vol., 13, No. 6, 1995, pp. 747-760.

Phadke, et al. "Laser-Assisted Deposition of Preformed Mesoscopic System" Materials Science and Engineering, C5, 1988, pp. 237-241.

Pique, et al. "Growth of Organic Thin Films by the Matrix Assisted Pulsed Laser Evaporation(MAPLE) Technique" Thin Solid Films, 1999, pp. 355-356 and 536-541.

Fluidization (Grace and Matsen, eds., Plenum Press, NY, 1980).

Agarwal, et al. "Laser Assisted Deposition of Supramolecular Organizates on Solid Surfaces" Materials Science and Engineering C6, 1998, pp. 13-17.

Sciarra, et al. Chapters 15 and 16 from Modern Pharmaceutics, pp. 605-671.

Burton, et al. "Absorption of Corticosteriods from the Rat Lung" Steroids, vol. 23, No. 5, 1974, pp. 617-624.

Conti, et al., "Use of Polylactic Acid for the Preparation of Microparticulate Drug Delivery Systems" J. Micorencapsulation, vol. 9, No. 2, 1992, pp. 156-166.

Fielding, et al. "Factors Affecting the Release Rate of Terbutaline from Liposome Formulations After Intrutrucheal Instillation in the Guinea Pig" Pharmaceutical Research, vol. 9, No. 2, 1992, pp. 220-223.

Glatt, "Multi-Purpose Fluid Bed Processing", Product Literature, 1988.

Göpferich, et al. "Development and Characterization of Microencapsulated Microsphere" Pharmaceutical Research, vol. 11, No. 11, 1994, pp. 1568-1574.

Herdan, G. "Small Particle Statistics" Second Edition, Butterworths, London, 1960.

Hochhaus, G. "Pharmacokinetic/Pharmocodynamic Aspects of Aerosol Therapy Using Glucocorticoids as a Model" J. Clin. Pharmacol. 1997; 27 pp. 881-882.

Hochhaus, et al. "Assessmen of Glucocorticoid Lung Targeting by ex-Vivo Receptor Binding Studies in Rats" Pharmaceuitical Research, vol. 12, No. 1, 1995, pp. 134-137.

Kawashima, et al. "A New Powder Design Method to Improve Inhalation Efficiency of Pranlukast Hydrate Dry Posder Aerosois by Surface Modification with Hydroxypropylmethylcellulose Phthalate Nanospheres" Pharmaceutical Research, vol. 15, No. 11, 1998, pp. 1748-1752.

Kodas, et al. "Aerosol Processing of Materials" Wiley-VCH, New York, 1999.

Mathiowitz, et al. "Biologically Erodable Microspheres as Potential Oral Drug Delivery Systems" Nature, vol. 386, 1997, pp. 410-414.

Newman, et al. "Efficient Delivery to the Lungs of Flunisolide Aerosol From a New Portable Hand-Held Multidose Nebulizer" Journal of Pharmaceutical Sciences, vol. 85, No. 9, 1996, pp. 960-964.

Ogale, S.B., "Deposition of Polymer Films by Laser Ablation" Chatper 25, pp. 567-579.

Schrier, et al. "Pulmonary Delivery of Liposomes" Journal of Controlled Release, 24(1993), pp. 209-223.

Takenaga, et al. "Microparticle Resins as a Potential Nasal Drug Delivery System for Insulin" Journal of Controlled Release, 52, 1998, pp. 81-87.

Tremblay, et al. "Liposomal Dexamethasone Effectiveness in the Treatment of Hypersensitivity Pneumonitis in Mice" European Journal of Clinical Investigation (1993), 23, pp. 565-661.

Vidgren, et al. "A Study of 99m Technitium-labeled beclomethasone dipropionate dilauroylphosphatidylcholine liposome aerosol in normal voluteers" International Journal of Pharmaceuitics 115, 1995, pp. 209-216.

Zeng, et al. "The Controlled Delivery of Drugs to the Lung" International Journal of Pharmaceutics, 124, 1995, pp. 149-164.

Schrier, et al., "Thermodynamic and Kenetic Aspects of the Interaction of Triamcinolone Acetonide with Liposomes", Proceed, Intern. Symp. Control. Rel. Bioact. Mater., 21 (1994, pp. 228-229.

Mutschler, et al., "Basic Principles and Therapeutic Aspects" Drug Actions, 1995, pp. 286-287.

Manekar, et al. "Microencapsulation of Propranolol Hydrochloride by the Solvent Evaporation Technique" Microencapsulation, 1992, vol. 9, No. 1, pp. 63-66.

Huang, et al., "An AMI-based Model for the Estimation of the Relative Binding Affinity for Glucocorticoids", 1st Drug Optimization via Retrometabolism Conference, Amelia Island: Die Pharmazie 1997, pp. S23.

Leach, et al. "Oligolactic Acid (OLA) Biomatrices for Sustained Release of Asthma Therapeutics" Respiratory Drug Delivery VII, 2000, pp. 75-81.

* cited by examiner

1) Mounting post
2) Adjustment post
3) Rotation motor
4) Target Mount
5) Target

METHODS FOR PREPARING COATED DRUG PARTICLES AND PHARMACEUTICAL FORMULATIONS THEREOF

The present application claims the benefit of PCT Application No. PCT/US99/27401, filed on Nov. 18, 1999, which claims the benefit of U.S. Provisional Patent Application No. 60/110,291, filed on Nov. 30, 1998, and U.S. Provisional Patent Application No. 60/108,847, filed on Nov. 18, 1998, which are all incorporated herein by reference.

1. BACKGROUND OF THE INVENTION

1.1 Field of the Invention

In general, the invention relates to drug particles or drug delivery particles coated with a biodegradable or biocompatible material, such as a polymer, to control surface properties, drug diffusion rates and release rates. More particularly, the invention provides methods for preparing pharmaceutical compositions that are coated with ultrafine layers of organic polymeric coating materials applied through the non-aqueous, non-solvent technique of vapor deposition processes such as pulsed laser ablation. Among the many advantages of the disclosed methods are control of coating both the thickness and uniformity of the coating onto the surfaces of the selected particulate drug.

1.2 Description of Related Art

Currently, aqueous/solvent (wet/sol) techniques are used to produce polymeric coatings onto particulate materials (Zeng, 1995). Poly(lactic acid) (PLA), poly(glycolic acid) (PGA), and their copolymers poly(lactic-co-glycolic acid) (PLGA) have been used to create microspheres that are currently being researched for pulmonary drug delivery of several drugs, but common solvent-evaporation techniques produce low encapsulation efficiencies (1–10%) and complicated processing (Talton, 1999). Unfortunately, the present methods of applying these coatings onto particles for pulmonary drug delivery have not yet effectively achieved particles in the micron size range.

Dry-powder inhalers (DPI) are used to deliver various drugs to the lungs for either localized or systemic delivery (Zeng, 1995). Although the current drug delivery systems are moderately efficient for pulmonary drug administration, they are limited by potential problems with pulmonary deposition characteristics as well as the release-rate kinetics of the drug after inhalation (Hochhaus, 1997).

Nanocapsule and microsphere formulations that are well known in the pharmaceutical arts have been typically inefficient in delivering drugs to the pulmonary surface via inhalation, and control of the particle size and coating thicknesses have been problematic. Similar shortcomings have been encountered using liposomal formulations to coat drug particles.

1.3 Deficiencies in the Prior Art

As noted above, the prior art methods are lacking in many respects for the preparation of coated drug particles that are optimized for aerosol and inhalation therapies. Only limited reports have used pulsed laser deposition to deposit polymeric nano-particle coatings on flat surfaces (Hansen, 1988; Blanchet, 1993; Li, 1998; Suzuki, 1998), and none have reported coatings on particles. Likewise, prior deposition methods have been largely unable to reproducibly prepare ultrafine-coated drug properties with sufficient pharmaceutical activity to make them useful for aerosol delivery of drugs to the pulmonary surfaces of an animal lung. The most severe limitations of the prior art methods include low encapsulation efficiency, long processing times, and porosity from solvent evaporation (Talton, 1999).

Therefore, what is needed are improved methods for preparing ultrafine coated drug particles that do not suffer these limitations, and that are useful in preparing pharmaceutical formulations with superior drug delivery and efficacy properties. Particularly lacking are methods for the preparation of medicaments that comprise coated drug particles of a size and functionality that are useful for aerosol or other pulmonary delivery.

2.0 SUMMARY OF THE INVENTION

The present invention overcomes these and other inherent deficiencies in the prior art by providing novel coating methods for use in preparing coated particles, and in particular, coated drug particles for having improved pharmaceutical properties and enhanced bioavailability characteristics. In general the methods disclosed herein provide a means for coating host or core particles with one or more layers of discrete coating particles such that the coated particles adhere generally uniformly to the surface of the host particles to form either continuous or discontinuous coatings depending upon the particular application of the coated particles.

2.1 Methods for Preparing Coated Drug Particles

The method of the present invention involves physical vapor deposition (PVD) of the polymer coating onto the surface of the target particle. Means for achieving PVD are well-known in the art, and include such methods as thermal evaporation, sputtering, and laser ablation of a target material to produce a flux of coating particles, which are then contacted with the host particles, and allowed to form a coating thereon. Depending upon the amount of vapor or the length of deposition, the number of coating particles, and the thickness of the resulting layer of coating onto the host particle can be varied to achieve the particular objectives of a given coating process.

In the coating of drug particles, the inventors have developed the use of PLD or pulsed laser ablation in the preparation of ultrafine drugs having atomic to nanometric-sized particulate coatings that impart improved pharmaceutical properties to the resulting coated drugs. The present coating methods are particularly desirable, since the drug particles themselves are not subjected to conditions that would decompose, destroy, or alter the activity of the drug itself. The use of PLD also minimizes the thermal decomposition or denaturation of the coating material itself, and permits the deposition of the material onto drug particles that may be maintained at ambient temperature during the deposition process. Laser ablation is a substantial improvement over the thermal deposition and sputtering methods of the prior art that are often unsuitable for depositing organic polymer coatings onto organic or inorganic drug particles.

Through regulation of the physical parameters of the deposition process (including vapor pressure and coating exposure time) the skilled artisan may now for the first time prepare a variety of particulate drugs that comprise ultrafine particulate coatings. In particular, the method affords the control of both the extent of particulate coating, and the thickness of the resulting coating layer on the surfaces of the drug particles. Both relatively thick coating layers, and relatively thin coating layers may be produced by controlling the extent of laser ablation process and the exposure of the target particles to the coating vapor.

Likewise, to provide optimum deposition of the coating onto the surface of the drug particle, fluidization means or an agitation means may be employed to agitate the host particles during the coating process both to prevent agglomeration of the resulting coated particles, and also to control the extent of coating thickness onto the host particles. Such fluidization means may involve a physical stirring or alternatively may involve subjecting the target particles to a stream of air or gas or other fluid to agitate the particles during the vapor deposition process. The present method provides improved means for producing individual host particles that remain non-agglomerated after the deposition step.

The materials employed in the coating process are preferably materials such that when ablated by an energy source, comprise a vapor of discreet particles that are extremely small—typically preferred are coating particles that are sized on the order of from about 1 to 100 or so nanometers in average diameter. While the deposition materials employed in the preparation of coated drug particles may comprise an inorganic or an organic material, in preferred embodiments the inventors have found particular benefits in selecting an organic polymer for laser ablation and deposition onto the surface of pharmaceutical compounds. Particularly preferred as coating materials are organic compounds such as PLA, PGA, PLGA, and related polymers, and functionalized derivatives thereof.

The inventors have shown that these polymers may be readily deposited onto the surface of drug particles in preferred particle sizes and layer thicknesses using the laser ablation apparatus and method disclosed herein. This method may be used to deposit one or more layers of nanometric-sized coating (each on the order of from about 1 nm to about 1000 or so nm in thickness) on core particles that range on the order of from about 0.1 nm to about 500 nm in diameter. The average size of the resulting coated drug particles have been demonstrated on the order of from about 0.1 to about 500 $\mu$m or so in diameter.

Figure 1B:
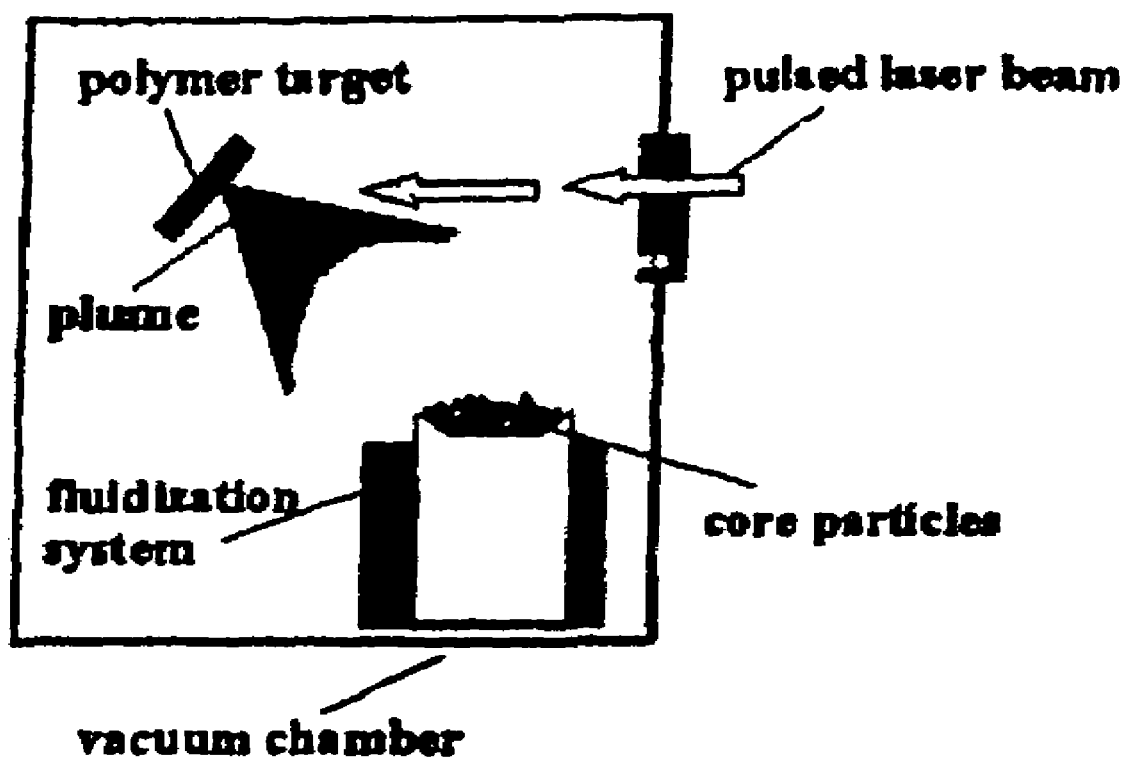

The PLD process for coating the drug particles of the present invention is illustrated in the text herein, and in the accompanying figures. For example. FIG. 1A and FIG. 1B show schematic diagrams of an illustrative experimental setup for PLD of coatings onto host particles. This setup includes a target and the particulate substrate contained within a vacuum chamber. The sealable chamber is provided so that the atmosphere within the chamber may be controlled as to the particular gases present and as to the partial pressure within the system using common technology. A laser beam enters the chamber through a suitably transparent window (such as quartz) and interacts with the target. The radiation from the laser is absorbed by the target material based upon its absorption coefficient. Due to the coupling of the laser photons with the target, the surface of the target material is rapidly heated and expands from the surface into the back-filled atmosphere in the form of a flux of ablated species called a plume. Due to collisions between neighboring atoms, polymer chains, and clusters, nano-particles form in flight that are then deposited onto the core particles, in this case the core is micronized drug particles. The polymer target may be rotated during the ablation process to avoid degradation effects and to ensure uniform ablation onto the surface of the host surfaces.

The host particles to be coated in the process may be mechanically fluidized to ensure coating uniformity during deposition. By controlling the background gas and pressure during deposition the coating thickness nano particle size and adhesion can be varied.

This coating method provides rapid thermal evaporation from the pulsed eximer laser to coat solid materials onto particles (Fitz-Gerald, 1998). Through this method, the coating material is generally less than 1% by mass, and coating times are under one hour without the need for drying solvents.

This variation of PLD uses high-energy pulses of ultraviolet light to deposit solid coating materials onto particles. Previously there has been a significant emphasis given to control of the particle characteristics (shape, size, surface chemistry, adsorption, etc.), but little attention has been on designing the desirable properties at the particulate surface, which can ultimately lead to enhanced properties of the product (Fitz-Gerald, 1998). By depositing atomic to nanometric-sized organic or inorganic, multi-elemental particles either in discrete (discontinuous) or continuous form onto the surface of the core particles, materials and products with significantly enhanced properties can be obtained. This process, known as the nano-functionalization of the particulate surface, provides ultrafine coated drug particles that have substantially improved phamaceutical properties when compared to the drug particles comprised within liposomal, nanocapsule or microparticle formulations of the prior art.

Through this coating method the coating material is generally less than 1% by mass, and coating times are under one hour without the need for drying solvents. This method has a wide variety of pharmaceutical applications ranging from coatings to improve agglomeration and flowability, stability, cell uptake and interactions, as well as controlling the release rate of the drug (Talton, 1999).

In an important embodiment, drug particles or drug delivery particles coated with biodegradable or bio-compatible polymer coatings with controlled thickness and controlled coating uniformity are produced using the Pulsed Laser Deposition (PLD) apparatus and methods as described herein. The drug particle coating thickness can be controlled down to nanometer thicknesses, and encapsulation can be partial or complete.

Host particles, which may range in size for example from several nanometers to several millimeters in diameter, are provided with a relatively uniformly dispersed discontinuous or continuous coating of discrete individual coating particles sized from atomic scale to a few nanometers. The coating particles are created by a PVD process, and preferably by laser ablation, where a pulsed laser beam is aimed at a target composed of the coating material under conditions sufficient to release individual particles from the target in a generally perpendicular ablation flux. PLD is especially suited for multi-elemental deposition in which the stoichiometry of the ablated species is maintained. This is particularly important when non-organic coating materials are employed. The size of the coating particles can be varied from atomic to nanometeric species by controlling the gas pressure used in the system during ablation. The chamber pressure can also be dynamically varied over time to control the agglomeration zones. During laser ablation, the host particles may be agitated or fluidized such that there is continual relative movement between all the host particles. The degree of coating is controlled by varying the laser parameters, energy density and number of pulses, gas pressure within the treatment chamber, and the treatment time.

In a preferred embodiment, there is provided a method of preparing coated drug particles and pharmaceuticals with a uniform coating as described herein. Such a coating may delay rug diffusion and dissolution until the coating degrades or until the drug diffuses through the coating for non-degradable coatings. The uniform coating may also be used to protect the drug particle from hostile environments. A partial coating controls the release rate due to surface area factors. The coating may also protect the drug particle size during processing steps such as compacted tablet grinding by providing a weaker interface that separates before the stresses fracture the drug particles themselves.

The coating may also improve aerodynamic and flow characteristics, which can be significant in determining the efficiency of drug delivery mechanisms.

2.2 Apparatus for Coating Particulates

The apparatus for providing thinly coated host particles comprises in general a vacuum chamber that allows delivery of an energy source, such as a laser, to a target material. The energy absorbed by the target results in ablation of material—the ablated material being of a scale in the range of nanometers or smaller—in a relatively high density flux in a controlled direction. Particles positioned within the area of the high-density flux will be coated by the target material. By fluidizing the particles, generally uniform coating will occur. One embodiment for fluidizing particles comprises rotation of an off-axis weight adjacent to the particle container. Another embodiment for the apparatus provides for continuous processing rather than batch processing by utilizing a feed hopper to deliver particles to a retention chamber, the retention chamber allowing movement of the particles in controlled manner through the coating area and into a removal conduit. It is preferable to provide heating means to heat the host particles during the coating steps.

In a preferred embodiment, the PVD technique known as laser ablation is employed in the fabrication of the coated particles. Laser ablation of a target material to produce free particles of the target material that adhere to a substrate is a well-known technique. Laser ablation is preferred since under optimized conditions the removal of species from the target takes place in a stoichiometric manner. When desirable, other PVD techniques, such as thermal evaporation or sputtering, may also be utilized to produce a flux of ablated species for deposition onto a host surface.

A typical laser used in the practice of the present method is a Lambda Physik model 305i pulsed excimer gas laser with an operating wavelength of 248 nanometers. Many other suitable lasers may be substituted therefor. The laser bean will produce a particle flux generally perpendicular to the surface of the target.

The laser wavelength is selected based on the nature of the material to be ablated. A high absorption coefficient and low reflectivity is necessary to remove the material efficiently by the ablation process. The absorption coefficient is dependent on the type of material and the laser wavelength and in some cases the intensity of the laser beam. Typically as the surface temperature is increased, the absorption coefficient of the material increases. Thus the selection of laser wavelenght is dependent on the type of materials ablated.

Additionally it is well known for those skilled in the art that the wavelegnths in the blue and ultravoilet region of the spectrum, the absorption coefficient increases and the reflectivity decreases. Thus although any wavelength could be used, the use of wavelengths less than 350 nm lead to more efficient removal of the material.

Since the laser system and the PLD chamber are separate, the process offers great latitude for varying experimental parameters. With the proper laser choice this process can be used to create coatings of many different materials on particulates. The composition of the coatings is strongly dependent on the laser processing parameters such as incident energy fluence (J/cm$^2$), laser repetition frequency, backfill gas pressure, target to substrate distance, and optical absorption coefficient of the target.

In most cases the chamber will be separate from the laser. However if one uses compact lasers like a solid-state laser operating from 248 to 1056 nm, the laser can be fitted inside the chamber. The specific conditions required for the deposition of coatings include (i) control of the laser fluence; (ii) control of the laser spot size; (iii) control of the gas; (iv) control over the pulsation rate; and (v) number of pulses and wavelength of the light. By controlling each of these parameters, which are different for different materials, the microstructure, topology, architecture, thickness and adhesion of the coatings on the drug particles can be varied.

2.3 Coated Drug Particle Composition's

The coating techniques described herein and the pharmaceutical compositions derived therefrom are applicable to a wide variety of drugs delivered to the lungs, such as anti-asthmatic drugs, biologically active peptides and proteins, and gene therapy related drug entities, as well as orally administered and parenteral administered drug particles as well.

In one embodiment, an oral drug is formulated with a thin-film coating of the present invention. Exemplary pharmaceuticals that would benefit from such a coating include drugs used in controlled or targeted release formulation, taste-masking, or particulate surface modification prior to tableting or capsule filling.

In another embodiment, a pulmonary drug is formulated with a thin-film coating of the present invention. Exemplary pulmonary drugs that could be used include glucocorticoids and other localized asthma drugs, as well as drugs and bioactive peptides and proteins for systemic delivery, such as insulin, that have low absorption through the oral route. In preferred embodiments, the glucocorticoids budesonide and tramcinolone acetonide (TA), as well as the antibiotic rifampicin have been shown to be particularly amenable to the processes of the present invention. When coated, these three drugs demonstrated excellent characteristics for improved inhalation delivery. The present methods provided a high encapsulation efficiency, reduced damage to the drug particle during coating, and did not produce coatings of a thickness that would reduce respiratory fraction.

Topical drugs that could be used include localized antibiotics, antifungals, and anti-inflammatories. Parenteral drugs that could be used include many currently used suspensions and preparations for sustained or localized release.

In illustrative embodiments, the coating material may be deposited onto the surface of the drug particle by a pulsed laser ablation process wherein the individual coating particles deposited onto the drug particles range in size from about 1 or 2 nm in average diameter up to and including about 40 or 50 nm or so in diameter. More preferably the particles that comprise the coating may be range in size from about 3 or 4 nm in diameter up to and including about 20 to 30 nm or so in diameter. In other embodiments the particles that comprise the coating may be range in size from about 5 or 6 nm or so in diameter up to and including about 10 to 15 nm or so in diameter. Indeed the inventors contemplate that particle sizes such as about 1, about 2, about 3, about 4, about 5, about 6, about 7, about 8, about 9, about 10, about 11, about 12, about 13, about 14, about 15, or about 16 nm in diameter may readily be prepared using the present methods, and may be used to coat drug particles in layers ranging from about 5 to about 1000 nm or so in thickness. Such layers may not be necessarily continuous in thickness over the entire surface of the drug particles, but may provide an average coating thickness that falls within such ranges. Likewise, the inventors contemplate that particle sizes such as about 17, about 18, about 19, about 20, about 21, about 22, about 23, about 24, about 25, about 26, about 27, about 28, about 29, about 30, about 31, or about 32 nm in diameter may also be prepared using the present methods, and such coating particles may also be used to coat drug particles in layers ranging from about 5 to about 1000 nm or so in thickness. Such layers may not be necessarily continuous in thickness over the entire surface of the drug particles, but may provide an average coating thickness that falls within such ranges. In similar fashion, by modifying the particular parameters of the coating process, it may be desirable to provide coatings that are comprised of particles of slightly larger average diameter particle sizes. As such, the inventors also contemplate that particle sizes such as about 33, about 34, about 35, about 36, about 37, about 38, about 39, about 40, about 41, about 42, about 43, about 44, about 45, about 46, about 47, about 48, about 49, about 50, about 51 or even about 52 or so nm in diameter may also be useful in coating particular drug particles for use in the pharmaceutical arts. As described above, such layers do not necessarily have to be continuous in thickness over the entire surface of the drug particles, and in fact, in certain embodiments, it may be more desirable to provide substantially discontinuous deposition of the coating particles onto the surfaces of the drug particles to achieve coated drug particles that have particular pharmaceutically-desirable properties. In some cases, it may even be highly desirable to provide coatings that are almost entirely discontinuous in thickness over the surfaces of the drug particles. Likewise, in certain applications, it may also be desirable to coat the drug particles with mixtures of two or more coating materials. Such coating mixtures may be prepared so that each member of the plurality of coating materials may be simultaneously ablated and applied to the surfaces of the drug particles, or more conveniently, it may be desirable to alternate or sequentially apply two or more coating materials onto the surface of the drug particles to be coated. The ability of the method to prepare pluralities of layers of coating materials is particularly desirable when time-control- or sustained-release formulations are being prepared. Such combinations of coating materials may afford particular pharmaceutically desirable properties to the resulting coated drug particles.

The choice of host particle size, the choice of coating material(s), the size of the coating material particles, and the overall and continuous/discontinuous nature of the coating layer(s) will, of course vary from particular application to application, and the skilled artisan will be able to adjust such parameters to prepare coated drug particles having particular desired physical or pharmaceutical properties. The choice of these parameters will often depend upon the particular compound to be coated, and/or the particular coating to be applied to the host particle. Likewise, the preparation of the host particle may be varied depending upon the particular thickness of coating to be applied during the laser ablation process. In some circumstances, it may be necessary to dessicate, grind, pulverize, or otherwise reduce the particular host particles to a certain uniform particle size or consistency prior to, or following, the deposition of the coating material(s) onto the surfaces of the host drug particles. In either embodiment, the milling of the coated or uncoated drug particles may be readily achieved using methods well known to those of skill in the pharmaceutical arts. For example, mechanical shearing or milling may be used to reduce the particles to a particular average particle size. Likewise, methods such as sieving may be employed to improve the uniformity of particle particle sizes in a given sample.

When desirable, no milling or sizing may be required, and in fact, the drugs to be coated may be subjected to the laser ablation processes described herein in their natural, or commercially-available state. Moreover, in some situations, it may not even be necessary to assure a particular coating particle size or a coating thickness, or even to prepare substantially continuous layers of coating material onto the surface of the drug particle, so long as the resulting coated material retains all or most of its desired characteristics.

As described above, the layer(s) of coating material(s) to be deposited onto the surface of the drug particle may range in average thickness from about 5 nm to about 1000 or so nanometers. In certain embodiments, the coating particles will form one or more layers onto the surface of the drug particles, each layer having a thickness of about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 or so nm. In other embodiments, slightly thicker coating layers will be desired and in those instances, layers having an average thickness of about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60 or so nm may be useful in coating particular drug particles for use in the pharmaceutical arts. Likewise, when slightly thicker coating layers are required, layers having an average thickness of about 65, about 70, about 75, about 80, about 85, about 90, about 95, about 100, about 120, about 140, about 160, about 180, about 200, about 225, about 250, about 275, about 300, about 400, about 450, about 500, about 550, about 600, about 650, about 700, about 750, about 800, about 850, about 900, about 950, about 1000, or even about 1025 or 1050 or so nm may be useful in coating particular drug particles for use in achieving coated drug particles having certain pharmaceutically desirable properties.

As described herein, the sizes of the host drug particles to be coated may range in average diameter from about 0.1 nm to about 500 or so nanometers. In certain embodiments, the host drug particles will typically have an average size of about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, or about 20 or so nm in average particle diameter. For some drugs, the average particle diameter size may be slightly larger. As such, the method may also be employed to coat these particles as well. In these instances, the drug particles may have an average particle size of about 21, about 22, about 23, about 24, about 25, about 26, about 27, about 28, about 29, about 30, about 40, about 50, about 60, about 70, about 80, about 90, about 100, about 120, about 140, about 160, about 180, about 200, about 220, about 240, about 260, about 280, about 300, about 350, about 400, about 450, or even about 500 or so run in diameter. In all cases, the inventors contemplate that all intermediate sizes in each of the stated size ranges may be prepared using the disclosed methods, and consider such intermediate sizes to fall within the scope of the present invention.

The coated drug particles of the present invention may range in size from about 0.1 $\mu$m average diameter, up to and including those coated particles that are about 1000 $\mu$m or so in average particle size diameter. As described herein, the sizes of the coated drug particles may range in average diameter sizes of from about 0.2 µm to about 800 or so µm. In certain embodiments, the final coated drug particles obtained following pulsed laser ablation of the coating material onto its surfaces will typically have an average particle diameter size of about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, or about 20 or so µm. For some drugs, the average coated drug particle diameter size may be slightly larger, and may have an average size of about 21, about 22, about 23, about 24, about 25, about 26, about 27, about 28, about 29, about 30, about 40, about 50, about 60, about 70, about 80, about 90, about 100, about 120, about 140, about 160, about 180, about 200, about 220, about 240, about 260, about 280, about 300, about 350, about 400, about 450, about 500, about 550, about 600, about 650, about 700, about 750, about 800, about 850, about 900, about 950, about 1000, or even about 1050 or so µm in average diameter. In all cases, the inventors contemplate that all intermediate sizes in each of the stated size ranges may be prepared using the disclosed methods; and consider such intermediate sizes to fall within the scope of the present invention.

2.4 Pharmaceutical Formulations comprising Coated Drug Particles

The present invention also concerns formulation of one or more of the coated drug particle compositions disclosed herein in pharmaceutically acceptable solutions for administration to a cell or an animal, either alone, or in combination with one or more other drugs for the treatment of particular diseases or medical conditions.

The coated drug particle compositions disclosed herein may be administered in combination with other agents as well, such as, e.g., proteins or polypeptides or various pharmaceutically-active agents. As long as the composition comprises at least one of the coated drug particle compositions disclosed herein, there is virtually no limit to other components that may also be included, given that the additional agents do not cause a significant adverse effect upon contact with the target cells or host tissues. The disclosed compositions may thus be delivered along with various other agents as required in the particular instance. Such secondary compositions included in the pharmaceutical formulations may be purified from host cells or other biological sources, or alternatively may be chemically synthesized as described herein. The formlations may comprise substituted or derivatized RNA, DNA, or PNA compositions, they may also be modified peptide or nucleic acid substituent derivatives, or other coated or non-coated drugs.

The formulation of pharmaceutically-acceptable excipients and carrier solutions are well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

2.4.1 Oral Delivery

The pharmaceutical compositions disclosed herein may be delivered via oral administration to an animal, and as such, these compositions may be formulated with an inert diluent or with an assimilable edible carrier, or they may be enclosed in hard- or soft-shell gelatin capsule, or they may be compressed into tablets, or they may be incorporated directly with the food of the diet.

The coated drug particle-containing compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instances tablets, pills, or capsules may be coated with shellac, sugar or both. A syrup or elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual formulation. For example, a mouthwash may be prepared incorporating the active ingredient in the required amount in an appropriate solvent, such as a sodium borate solution (Dobell's Solution). Alternatively, the active ingredient may be incorporated into an oral solution such as those containing sodium borate, glycerin and potassium bicarbonate, or dispersed in a dentifrice, including: gels, pastes, powders and slurries, or added in a therapeutically effective amount to a paste dentifrice that may include water, binders, abrasives, flavoring agents, foaming agents, and humectants, or alternatively fashioned into a tablet or solution form that may be placed under the tongue or otherwise dissolved in the mouth.

2.4.2 Injectable Delivery

Alternatively, the pharmaceutical compositions disclosed herein may be administered parenterally, intravenously, intramuscularly, or even intraperitoneally as described in U.S. Pat. No. 5,543,158, U.S. Pat. No. 5,641,515 and U.S. Pat. No. 5,399,363 (each specifically incorporated herein by reference in its entirety). Solutions of the active compounds as free-base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The drug compositions to be coated by the methods disclosed herein may be formulated either in their native form, or in a salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

2.4.3 Nasal Delivery

The administration of the pharmaceutical compositions by intranasal sprays, inhalation, and/or other aerosol delivery vehicles is also contemplated. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety), and delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

2.4.4 Additional Modes of Drug Delivery

In addition to the methods of delivery described above, the following techniques are also contemplated as alternative methods of delivering coated drug particle compositions. Sonophoresis (i.e., ultrasound) has been used and described in U.S. Pat. No. 5,656,016 (specifically incorporated herein by reference in its entirety) as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. No. 5,770,219 and U.S. Pat. No. 5,783,208), and feedback-controlled delivery (U.S. Pat. No. 5,697,899), each specifically incorporated herein by reference in its entirety.

The delivery of aerosol formulations of the drugs of the present invention may be accomplished using methods such as those described in U.S. Pat. No. 5,849,265 and U.S. Pat. No. 5,922,306 (each specifically incorporated herein by reference in its entirety).

Particularly preferred medicaments for administration using aerosol formulations in accordance with the invention include anti-allergics, bronchodilators, and anti-inflammatory steroids used in the treatment of respiratory disorders such as asthma and the like.

Medicaments which may be coated and administered in aerosol formulations according to the present invention include any drug useful in inhalation therapy which may be presented in a form which is substantially completely insoluble in the selected propellant. Appropriate medicaments may thus be selected from, for example, analgesics (codeine, dihydromorphine, ergotamine, fentanyl, morphine and the like); anginal preparations; antiallergics (cromoglycate, ketotifen, nedocromil and the like); anti-infectives (cephalosporins, penicillins, rifampicin, streptomycin, sulfonamides, macrolides, pentamidines, tetracyclines and the like); antihistamines (methapyrilene and the like); anti-inflammatories (flunisolide, budesonide, tipredane, triamcinolone acetonide, and the like); antitussives (noscapine and the like); bronchodilators (ephedrine, adrenaline, fenoterol, fomioterol, isoprenaline, metaproterenol, phenylephrine, phenylpropanolamine, pirbuterol, reproterol, rimiterol, terbutaline, isoetharine, tulobuterol, orciprenaline, and the like); diuretics (amiloride and the like); anticholinergics (ipratropium, atropine, oxitropium and the like); hormones (cortisone, hydrocortisone, prednisolone and the like); xanthines (including aminophylline, choline theophyllinate, lysine theophyllinate, and theophylline); and therapeutic proteins and peptides (e.g., insulin or glucagons).

One of ordinary skil in the art will appreciate that in certain circumstances, the coated drugs particles of the present invention may be formulated in the form of salts (such as alkali metal or amine salts or as acid addition salts) or as esters (e.g., lower alkyl esters) or as solvates (e.g., hydrates) to optimize the activity and/or stability of the medicament and/or to minimize the solubility of the medicament in the delivery vehicle or propellant.

It will be appreciated by those skilled in the art that the aerosol formulations according to the invention may, if desired, contain a combination of two or more active ingredients. Aerosol compositions containing two active ingredients (in a conventional propellant system) are known, for example, for the treatment of respiratory disorders such as asthma. Accordingly the present invention further provides aerosol formulations that contain two or more particulate medicaments that are coated using the methods of the present invention. The medicaments may, be selected from suitable combinations of the drugs mentioned herein, such as budesonide (BUD), triamcinolone acetonide (TA), fluticasone propionate (FP), and the like, or may even include suitable combinations of other bronchodilatory agents (including ephedrine and theophylline, fenoterol, ipratropium, isoetharine, phenylephrine, and the like).

Preferred aerosol formulations in accordance with the invention comprise an effective amount of a polymer-coated particulate pulmonary medicament and a fluorocarbon or hydrogen-containing chlorofluorocuarbon propellant. The final aerosol formulation may typically contain from about 0.005% to about 10% (wt./wt.) of the coated drug particles, more preferably from about 0.05% to about 5% (wt./wt.) of the coated drug particles, and more preferably still, from about 0.1% to about 3.0% (wt./wt.), of the coated particles relative to the total weight of the formulation.

The propellants for use in the invention may be any fluorocarbon or hydrogen-containing chlorofluorocarbon or mixtures thereof as described in U.S. Pat. No. 5,922,306.

2.5 Coating Compositions

The target materials used for the coating include most solids currently used in the pharmaceutical and food industries, namely any material that can be effectively ablated by the energy source. These materials include, but are not limited to, biodegradable and biocompatible polymers, polysaccharides, and proteins. Suitable biodegradable polymers include PLA, PGA, PLGA, and other polylactic acid polymers and copolymers, polyorthoesters, and polycaprolactones, etc. Suitable biocompatible polymers include polyethyleneglycols, polyvinylpyrrolidone, and polyvinylalcohols, etc. Suitable polysaccharides include dextrans, cellulose, xantham, chitins and chitosans, etc. Suitable proteins include polylysines and other polyamines, collagen, albumin, etc.

2.6 Substrates for PLD Coating

The host or core particles are generally large relative to the size of the coating particles, with the method proven to be very applicable to host particles sized from 0.5 to 100 microns. It is understood that the host particles can be smaller, down to several nanometers in diameter, or larger, up to several millimeters in diameter, than this range if so desired. The host particles are retained within a processing container that has a large enough volume to permit movement of the particles within the container. The top of the container is open and the container maintained in a vertical position during fluidization, or a portion of the processing container, such as a part or all of a side or bottom, is provided with openings or apertures to retain the host particles within the processing container, if the particle deposition is to occur laterally or from below.

A suitable construction for the processing container has been found to be a cylindrical glass vial with one open end, the open end being covered, if necessary, by a wire mesh or screen with apertures slightly smaller than the size of the host particles. The processing container is mounted within the treatment chamber with the open end facing the target at a distance of from approximately 3 to 10 centimeters such that the majority of particles in the perpendicular flux from the target will enter the processing container and contact the host particles. The system may also be constructed with continuous or incremental transport means for the host particles, such as a conveyor system, whereby the host particles can be moved relative to the ablation flux during the coating process so that coating may occur in a continuous manner.

The host particles must be agitated or fluidized in some manner to expose the entire surface of each host particle to the coating particles entering the processing container to insure general uniformity of coating and to assist in the prevention of agglomeration of individual host particles. This fluidization may be accomplished in a number of equivalent manners, such as by mechanical agitation by vibration, rotation or movement of the processing container, by providing a stirring device within the container, or by pneumatic agitation by passing gas flow through the host particles. Another means to accomplish the required fluidization is to intermix magnetic particles, such as iron, with the host particles and then to apply an alternating magnetic field to the processing container during the deposition of the coating particles. The magnetic particles are separated from the host particles after the treatment process.

The percentage of deposition or coverage of the coating particles on the host particles is controlled by controlling the size of the coating particles and the treatment time. The longer the treatment time, the more coating particles will be adhered to the surface of the host particles, increasing both the percentage of coverage and the thickness of the coating layer. Surface coverage can be adjusted from below 1 percent up to 100 percent. The size of the coating particles is controlled by the atmospheric composition and partial pressure within the treatment chamber. By dynamically controlling the gas pressure the reaction zone for forming the coating particles can be controlled. Reactive gases such as oxygen, ammonia or nitrous oxide produce higher concentrations of molecular, as opposed to atomic, species within the ablated particle flux, and are used if deposition of oxide, nitride or similar particles is desired. Pressure within the chamber determines the number of collisions between ablated coating particles, with higher pressure causing more collisions and therefore larger coating particles in the ablated flux. Pressure within the system may vary greatly, from $10^{-10}$ to 10 Torr for example, but production of 1 to 10 nanometer or smaller coating particles typically occurs at approximately 400 mTorr or higher. For the production of atomic sized coating particles, the pressure employed is typically at or below approximately 300 mTorr.

The particulate species coated using this method include many substrates, including drugs used for oral, pulmonary, topical, and parenteral administration. The substrates suitable for coating may be drug particles of various sizes ranging from <1 μm to >1 mm.

3.0 BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1A is a general illustration of the apparatus components.

FIG. 1B is a schematic representation of the PLD processing equipment used in coating the drug particles.

FIG. 2 is an illustration showing the adjustability of the target.

FIG. 3 is an illustration of a batch-processing set-up.

FIG. 4 is an illustration of a continuous processing set-up.

FIG. 5A and FIG. 5B show alternate heat sources for heating the host particles.

FIG. 6 shows the dissolution of coated vs. uncoated budesonide (BUD) in pH 7.4 PBS (50 mM, 0.5. % SDS) at 37 C (n=3). Coating times were 10 min 570 and 25 min•vs. uncoated budesonide powder ▲.

FIG. 7 shows the dissolution of coated vs. uncoated TA in pH 7.4 PBS (50 mM, 0.5% SDS) at 37 C (n=3). Coatings were at 2 hertz ▲ and 5 hertz• vs. uncoated TA powder ■.

FIG. 8 shows the dissolution of coated vs. uncoated Rifampin (RIF) in pH 7.4 PBS (50 mM, 0.5% SDS) at 37 C (n=3). Coating was for 20 min vs. uncoated RIF powder

4.0 DESCRIPTION OF ILLUSTRATIVE EMBODIMENTS

4.1 Some Advantages of the Invention

Modification of (1) the aggregation characteristics; (2) the aerodynamic flow properties during deposition; and, (3) the release-rate of the drug in the lungs are possible by applying biodegradable coatings using the methods of the present invention to greatly enhance the deposition efficiency and pharmacokinetic profiles of drugs coated by the present methods.

Drugs coated by the processes outlined herein have been shown to possess high encapsulation efficiencies (>99% drug) while requiring minimal processing. The process also has several advantages over current techniques including:

1. It is a fast process with modification times (i.e. how long it takes to coat a powder from beginning to end) on the order of minutes.

In the laser process, by choosing a correct energy density, the material can be made to ablate in a more cluster-like form that retains some of the signature of the target species. When the energy density (fluence) is increased, the ablation has more of an atomic character, and is composed of atoms that do not resemble the signature of the original material.

2. A variety of materials can be used for producing the coatings on the particulate materials, thus it is possible to produce films from materials with proven biocompatibility.
3. It is a dry, solvent-less technique that can be conducted under a sterile environment, which is an important consideration in the drug industry.
4. Particle agglomeration/adhesion can be minimized by applying coatings that affect the bonding nature and electrostatic charge on the surface.
5. Formation of microcapsules by depositing coatings onto the particle surface will make it possible to control drug release kinetics by: (a) diffusion of the drug through the polymer; (b) degradation of the biodegradable polymer coating off of the drug particles, releasing the core drug material.

4.2 Particle Coating Apparatus

The apparatus disclosed herein offers significant improvements over the devices of the prior art by providing fluidization and coating of primary core particulate materials with target materials of choice. Target materials may include polymers, medical materials, metals, ceramics, semiconductors and tissue. The apparatus operates in low vacuum (mTorr–Torr range) and operates in principle via delivery from an energy source (electron beam, laser, UV light source or ion beam) to a target material that can exist in the liquid, solid or frozen state. The target material then interacts with the energy source, adsorption of energy occurs and subsequent evaporation, ablation, removal of portion of the target surface then take place. The geometry of this exchange is controlled such that the removed target material is then directed onto an area of coating potential (AOCP). Within this AOCP, a high-density flux (HDF) of the target material is present. FIG. 1A and FIG. 1B show the main components of the system, which are labeled. By controlling the input energy from the above stated sources and the atmosphere within which the process occurs, control over the HDF can be achieved by means of particle—collision physics (PCP). Before the three specific operation modes referred to above are presented, a sample operation of the apparatus will be presented with respect to FIG. 1A and FIG. 1B.

Heating and or cooling of the core particulate materials via UV lamps, resistance heaters, RF sources, electric wire mesh membranes, liquid nitrogen and cold fingers provides significant advancement over the powder properties as compared to particle coated in unheated or room temperature conditions. Heating and cooling of the core particles during deposition provides added control over the surface energy mechanisms of coating growth and adhesion at higher and or lower rates by such mechanisms as defusion, desorption, adsorption, growth modes, activation energy and local thermodynamic equilibrium. In addition, significant classes of ceramic, electronic and super-alloys and multi-component materials such as superconductors and phosphor materials can be synthesized in a 1-step process, eliminating a secondary heat treatment step. The added energy provided by the heating allows diffusion of complex materials during the process to reorient in both crystallographic and stoichiometric orders that cannot be accomplished during room temperature depositions. Organic materials such as polymers also have increased potential during in-situ heating of the core particles due to the added energy for reorientation and chain alignment to occur. Heating of the core particles does not only decrease steps in the forming of coated particles but it also allows the synthesis of novel materials that can form due to this non-equilibrium condition imposed by the heating of the core particle substrate and the nano particle flux.

The fact that the core particles are fluidized continuously through the AOCP enables the inventors to take advantage of the inherent high surface area of particulate materials. Due to the fact that the surface area varies from 1 $cm^2$ for a silicon wafer to $10^3$–$10^4$ $cm^2$ for particulate materials allows for the control over coating thickness to range from atomic to micron thick depending on the processing conditions as described. In comparison to deposition onto flat substrates, a ten min deposition may yield a 2-micron thick coating on a 2 cm×2 cm silicon substrate whereas on 1 gm of particulate material (1–10 micron), the thickness has bee shown to be on the order of 25 nanometers. Further control of the nano particle coating is realized due to nano particle formation and growth during the coating process that can also be controlled via laser energy, pressure, backfill gas molecular weight and time.

The laser enters a low vacuum unit that houses the target, optical windows and fixtures 1. The laser or energy source then interacts with the target material as previously described 2. The subsequent adsorption of the laser or energy source results in the creation of the plume or high-density flux (HDF) 3. By fixturing the target (FIG. 2) with the appropriate geometry the direction of the HDF can be controlled.

Figure 2:
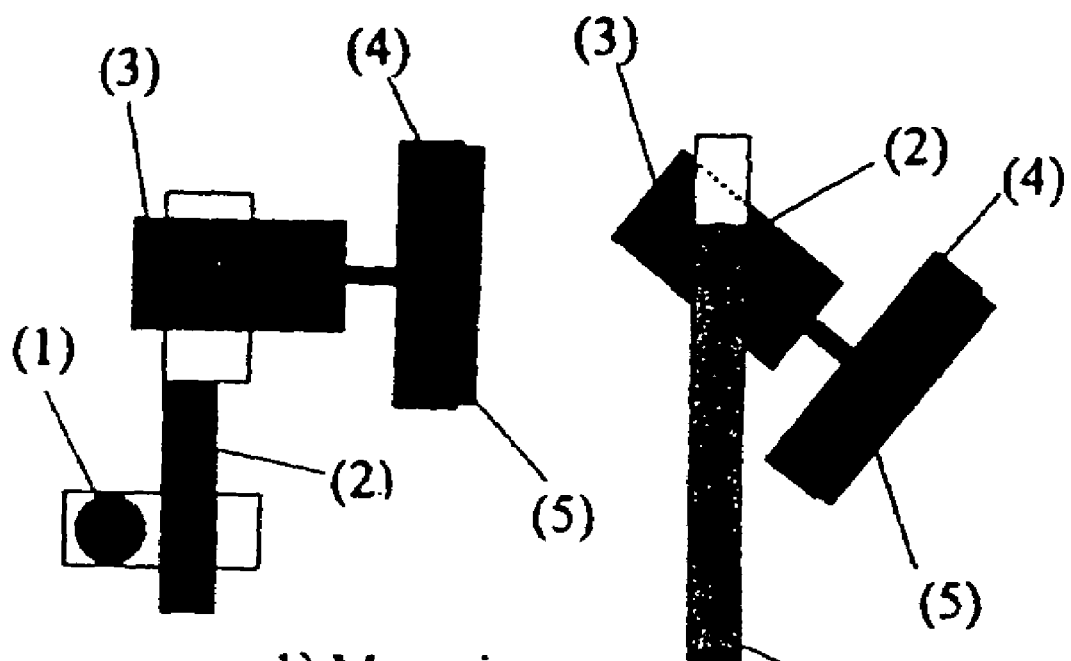
Figure 3:
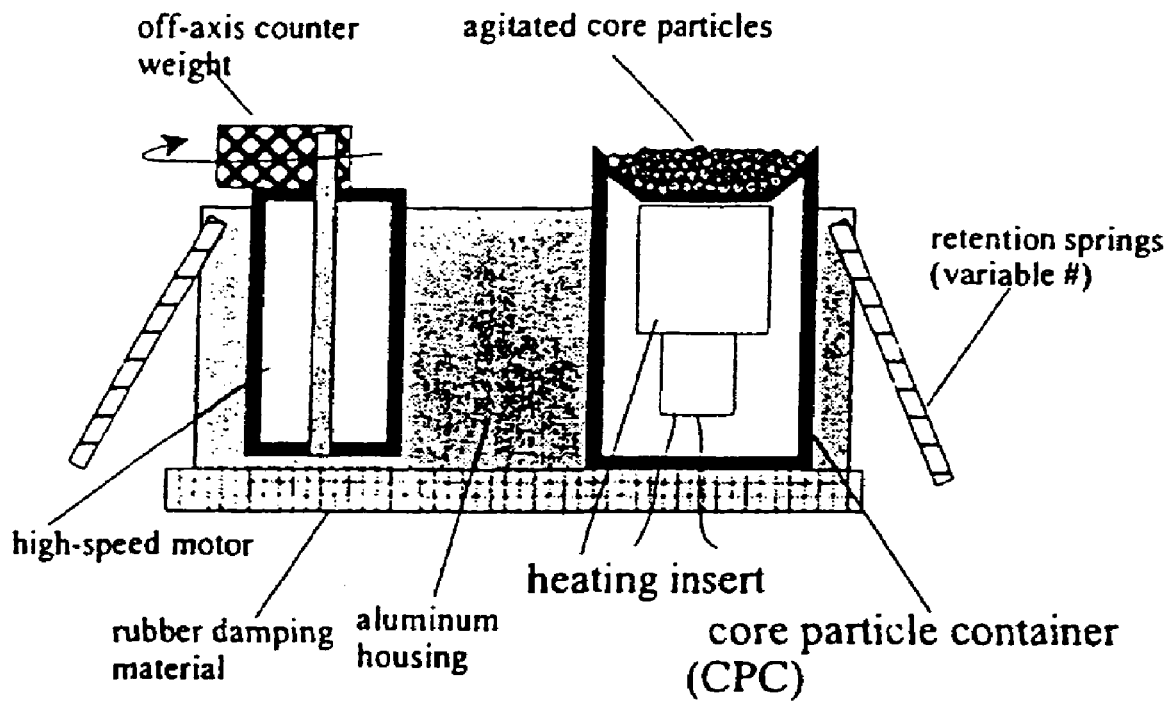

In a first operation embodiment, the batch process with heating capabilities is described. FIG. 1A, FIG. 1B and FIG. 2 are as previously described, with the exception that a mechanically agitated particle state (MAPS) is located within the AOCP. FIG. 3 illustrates the MAPS design and concept. The MAPS design utilizes and off-axis conterweight to create a range of frequencies and displacements that are then transferred to the core particle container (CPC) through an aluminum fixture as shown. By tuning the frequency of the system, proper agitation of the core particles can be obtained and maintained during the operation of the apparatus. The counterweight is made from 304 series stainless steel and is attached to the shaft of a rotating motor by two setscrews as shown. The motor, with the weight affixed is fastened within the aluminum housing as shown by additional fasteners. The vibrations are transferred to the CPC through the aluminum housing. The housing is isolated from the rest of the apparatus by rubber damping material and coil springs as shown. The heating block is located within the CPTS and can operate between 300–800 K if desired.

Figure 4:
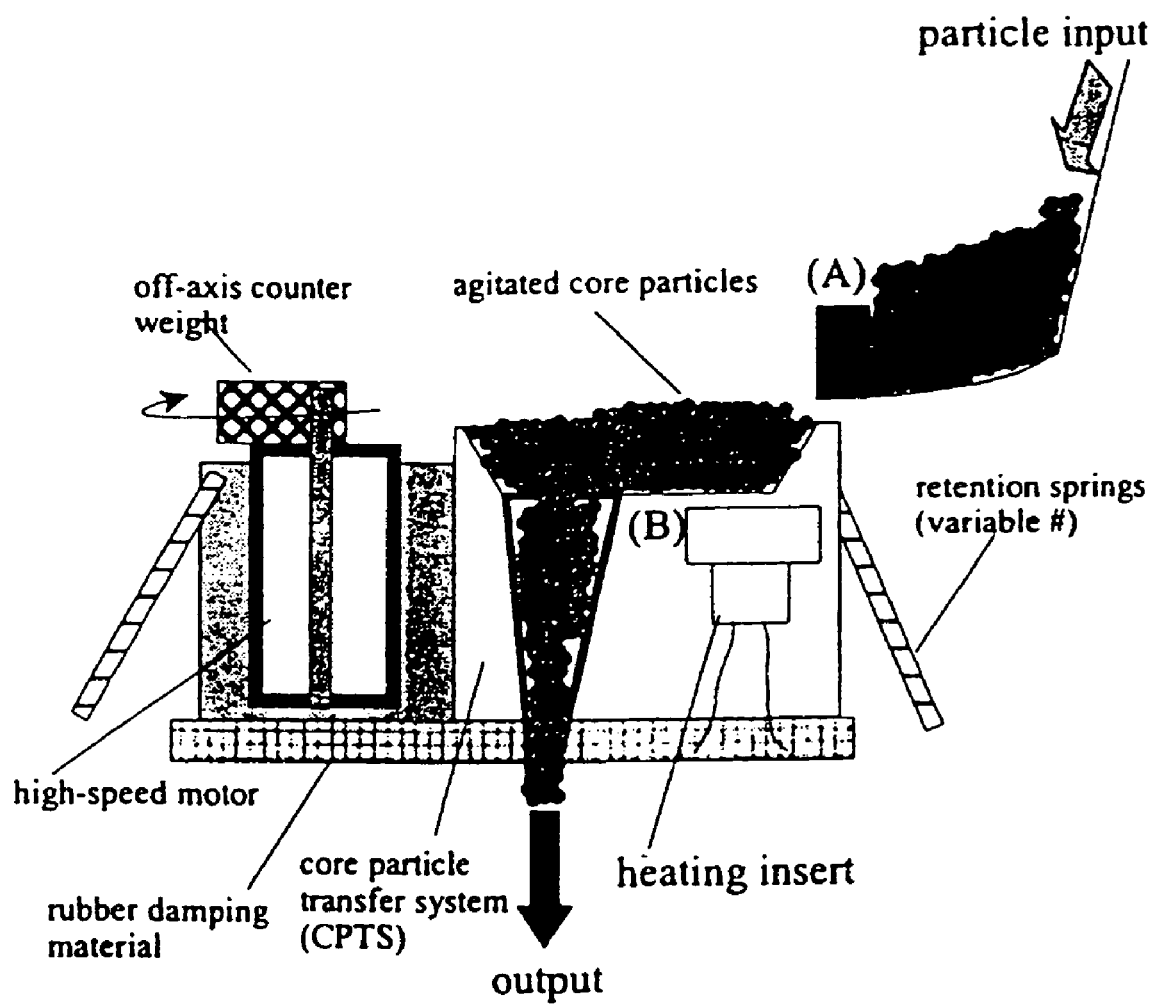

In a second operation embodiment, the continuous process with heating capabilities is described. FIG. 1A. FIG. 1B, and FIG. 2 are as previously described, and a mechanically agitated particle stage (MAPS) is located within the AOCP, as described in FIG. 4. The MAPS design utilizes an off-axis counterweight to create a range of frequencies and displacements that are then transferred to the core particle transfer system (CPTS) through an aluminum fixture as shown. By tuning the frequency of the system, proper agitation of the core particulates can be obtained and maintained during the operation of the apparatus, such that the time of exposure within the AOCP is controlled by movement of the particles from the input area to the output chute. The bottom of the exposure hopper may be slanted to facilitate single direction movement. The counterweight is made from 304 series stainless steel and is attached to the shaft of a rotating motor by two setscrews as shown. The motor, with the weight affixed is fastened within the aluminum housing as shown by additional fasteners. The vibrations are transferred to the CPTS through the aluminum housing. The housing is isolated from the rest of the apparatus by rubber damping material and coil springs as shown. Micro switches located at areas (A) and (B) operate the delivery and removal of the unprocessed/processed particulates. These micro switches will operate independently within the CPTS and can operate between 300–800° K. if desired.

Figure 5A:
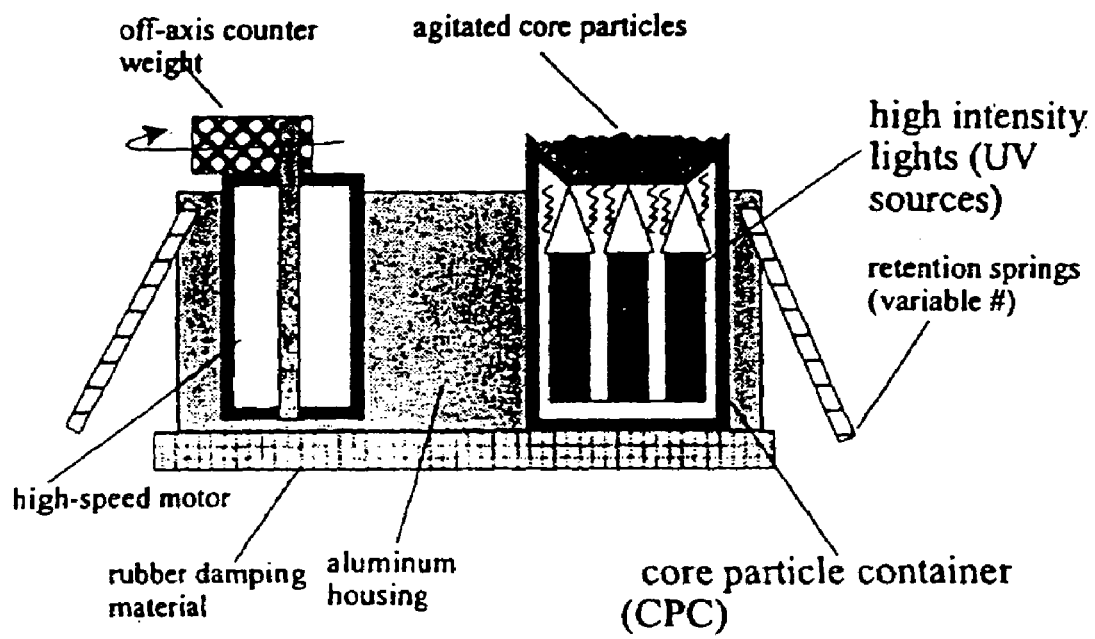
Figure 5B:
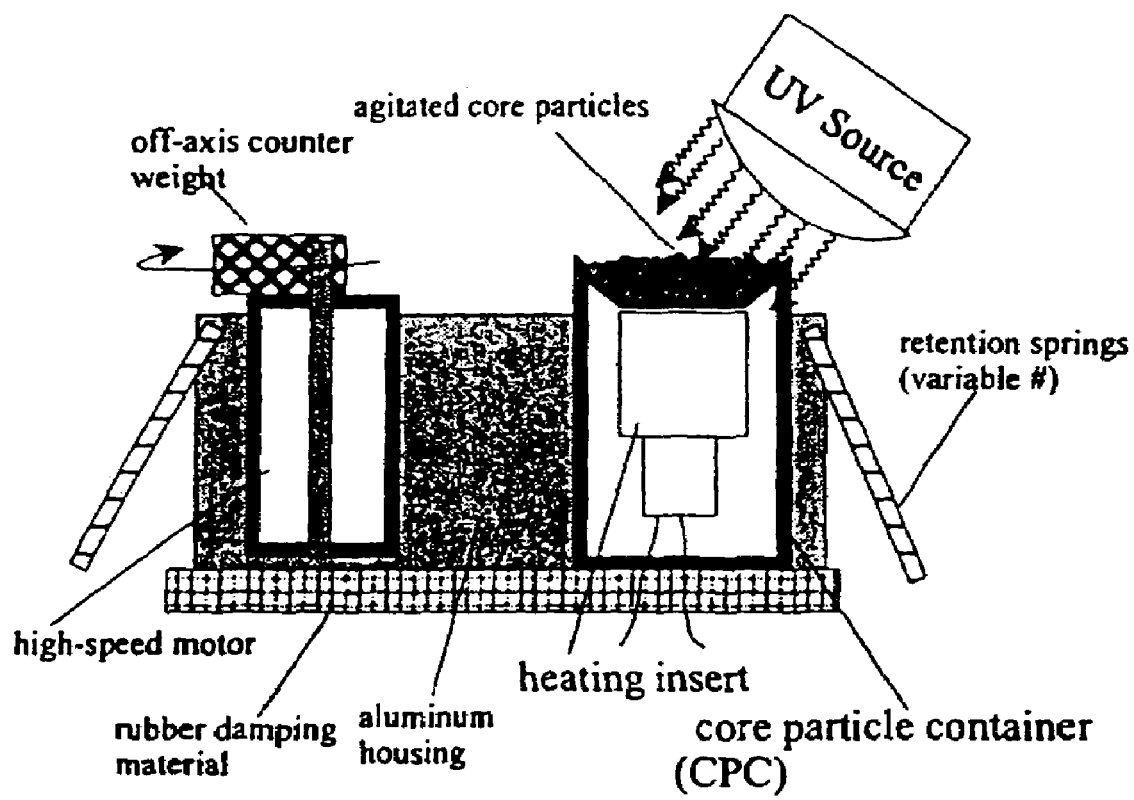

In a third operation embodiment, either the batch or continuous process described above may be utilized but with multiple and/or alternate particulate heating and/or target sources as shown in FIG. 5A and FIG. 5B. FIG. 5A illustrates the use of one or more UV-emitting heat sources for the CPC or CPTS. FIG. 5B illustrates the use of a combined UV heat source on top of and a heating source within the CPC or CPTS.

4.3 Glucocorticoids

Glucocorticoids are beneficial in treating various pulmonary diseases, including asthma, sarcoidosis, and other conditions associated with alveolitis. Although systemic glucoconicoid therapy is effective in such conditions, prolonged administration carries the risk of toxicity and side effects (Mutschler and Derendorf, 1995). In attempts at reducing systemic side effects, several clinically efficacious glucocorticoids, including TA, are employed for delivery as aerosols.

In a recent study, it was shown that lung specificity is achieved when glucocorticoid suspensions are administered intratracheally. In contrast, lung targeting is not observed when a glucocorticoid solution is administered intratracheally, presumably because of the fast absorption of the lipophilic steroid (Hochhaus et al. 1995). This suggests that pulmonary targeting depends on slow release from the delivery form that results in a prolonged pulmonary residence time.

The use of liposomes has been suggested to provide sustained pulmonary release for various drugs including glucocorticoids such as beclomethasone diprorionate and dexamethasone (Tremblay et al., 1993; Fielding and Abra, 1992; Vidgren et al., 1995; Schreier et al., 1993). However, although liposomes have a high loading capacity for lipophilic glucocorticoids such as TA under equilibrium conditions, TA is rapidly released under non-equilibrium conditions from the liposome matrix upon dilution or administration (Schreier et al., 1994).

4.4 Asthma Therapy

With the recognition of asthma as a relapsing inflammatory process, inhaled glucocorticoids have become the first-line treatment in the therapy of chronic asthma (Barnes and Pedersen, 1993; Barnes, 1995; Brogden and McTavish, 1992).

Inhaled glucocorticoids are not free from systemic side effects when markers such as 24-hour plasma cortisol are monitored (Loennebo et al., 1996; Grahnen et al., 1994). The extent of potentially undesirable systemic side effects represents only, half of the problem, however, because the assessment of lung selectivity requires the evaluation of both local pulmonary and systemic effects. Although there is no question that inhaled glucocorticoids are effective in the treatment of asthma, pulmonary "efficacy" is difficult to quantify in humans. New inhaled glucocorticoids, with different pharmacokinetic and pharmacodynamic properties and improved delivery systems (such as dry powder inhalers) with improved pulmonary deposition, have been introduced on the market. Differences in their properties (including physico-chemical factors potentially affecting the pulmonary residence time) will affect pulmonary targeting by determining the pulmonary and systemic availability of the drug. To provide an applied framework to evaluate the importance of these factors on pulmonary selectivity, the inventors used a theoretical model that integrates physiologic aspects of pulmonary inhalation with pharmacokinetic and pharmacodynamic drug properties for the prediction of pulmonary and systemic effects. Receptor occupancy was selected as a surrogate marker because early work in cell systems found a close correlation between the extent of receptor occupancy and the extent of the biological response (Dahlberg et al. 1983; Beato et al. 1972: Diamant et al., 1975. Baxter et al., 1973). In addition, a direct relation between the receptor affinity of a glucocorticoid and the activity at the site of action (e.g., the skin blanching activity) has been demonstrated (Hochhaus, 1983; Druzgala et al. 1991). Contrary to a number of drug classes, pharmacologic desired and adverse effects of glucocorticoids are induced by the same receptors. Consequently, pulmonary selectivity has been defined by the degree in which the occupancies of pulmonary and systemic receptors differ.

4.5 Comparison of Inhaled Glucocorticoids

Currently available inhaled glucocorticoids are based on the 21-carbon atom cortisol structure with four rings, three six-carbon rings and a five-carbon ring. The synthetic antiinflammatory glucocorticoids are characterized by lipophilic moieties in the 16 and 17 position; $CH_3$, F or Cl moieties in the 6 and 9 positions; and/or double bound carbons in the 1,2 position. Other essential features include a ketone oxygen at the 3 position, an unsaturated bond between the 4,5 carbons, a hydroxyl group at the 11 position, and a ketone oxygen at the 20 position. By modifying the basic structure of glucocorticoids, it is possible to alter the affinity for the glucocorticoid receptor (GR) and plasma protein binding, modulate the metabolism pathway (oxidation or hydrolytic), and the tissue binding and clearance (Edsbaecker and Jendro, 1998).

Adequate characterization of the overall pharmacokinetic drug properties is a necessary prerequisite for comparing the pulmonary targeting. The time course of the pharmacological response is determined by both the concentration and time of free drug at the receptor site. Therefore, to assess the systemic exposure of the drug, it is important to observe the glucocorticoid concentration vs. time profile in the systemic compartment by monitoring the plasma levels. Three commercially available inhaled glucocorticoids, triamcinolone acetonide (TA), budesonide (BUD), and fluticasone propionate (FP), are described below.

4.6 Triamcinolone Acetonide (TA)

TA entered the asthma market as the Azmacort MDI by Rhone-Poulenc in 1992. Doses of 200–400 mcg/day (100 mcg/puff) at 2–4 times daily were recently shown to have comparable therapeutic effect in forced expiratory volume (Kelly, 1998b). The pulmonary deposition ratio from Azmacort MDI with spacer has been reported to be approximately 22% (Rohatagi el al., 1995). First-pass metabolism in the liver to less active metabolites accounts for the reduced oral bioavailability of 20–25% (Derendorf et al., 1995). Absorption of TA suspension in the lungs has been measured to be approximate 2 hours by the difference in half-lives of intravenous (1.4–2.0 hours) versus inhaled (3.6 hours) doses (Rohatagi et al., 1995; Möllmann et al. 1985).

TA, along with flunisolide, belongs to the second generation of glucocorticoids that show an increased receptor binding affinity (RBA=361) (Wuerthwein et al., 1992). Plasma protein binding for TA, similar to the other inhaled glucocorticoids, has been reported at 71% (Derendorf et al., 1995). TA has a volume of distribution of 100–150 L and has a mean residence time of 2.7 hours after intravenous administration (Derendorf et al., 1995; Rohatagi et al., 1995; Möllmann et al. 1985). Clearance of TA is 37.3 L/hr and the major metabolite of TA is 6-hydroxytriamcinolone acetonide, whereas triamcinolone (TC) is only a minor metabolite (Rohatagi et al., 1995; Möllmann et al, 1985).

Triamcinolone acetonide phosphate (TAP), a water-soluble prodrug that is rapidly metabolized to TA, has been used for IV administration in humans (Möllmann et al, 1985). TAP, which shows dose-dependent kinetics, has a plasma half-life of 3–4 min and releases active TA immediately. No unchanged ester is found in urine after IV administration, indicating a complete conversion of TAP prodrug to TA. In addition, the total body clearance of TAP exceeds the hepatic blood flow, indicating a large contribution of extrahepatic metabolism due to hydroysis in the plasma (Möllmann et al., 1985). Previously, it was shown that pulmonary administration of TAP in a sustained-release liposome formulation resulted in a higher pulmonary residence time, a prolonged pulmonary effect, and a higher lung to systemic drug ratio (Suarez et al., 1998).

4.7 Budesonide (BUD)

Budesonide recently entered the United States drug market as Pulmicort™ Turbohaler (Astra USA) as the first inhaled glucocorticoid dry powder system. Prescribed doses of 400–1600 mcg per day have been reported (Kelly, 1998b), with a pulmonary deposition ratio reported of 32% (16–59%) for the DPI and 15% (3–47%) for the MDI sold in Europe (Astra-USA, 1997). About 89% of an oral dose of budesonide undergoes first-pass metabolism resulting in an oral bioavailability of 11% (Thorsson et al., 1994).

Budesonide has a higher receptor binding affinity (RDA=935) than TA and a higher protein binding (88%) (Thorsson et al., 1994). Its volume of distribution at steady state is 183 L, indicating high tissue affinity. Budesonide is a drug with a very high hepatic extraction ratio and a high clearance (84 L/h) close to hepatic blood flow. The plasma half-life of budesonide is 2.8 hours and is approximately the same after intravenous and inhalation administration, reflecting a fast rate of dissolution and absorption in the lung (Ryrfeldt et al., 1982). Similarly. Thorsson et al. (1994) reported a $C_{max}$ of 3.5 nmol/L at 0.3 hour after inhalation via Turbohaler and a $C_{max}$ of 2.3 mmol/L at 0.5 h after inhalation via MDI, indicating dissolution of the dry powder is not rate limiting.

Budesonide has been shown to have fast dissolution rate in the lung of rats (Chanoine et al. 1991) and humans (Ryrfeldt et al. 1982). Thus, decreasing its pulmonary release by encapsulation in microspheres or liposomes is expected to improve the lung selectivity. The lung absorption rate of micronized budesonide in suspension was compared with that of budesonide in solution using isolated perfused rat lungs (Ryrfeldt et al., 1989) with only a marginal difference in lung absorption rate. However, when budesonide 21-palmitate was incorporated into liposomes, budesonide showed prolonged retention time (half-life=6 hr) after intratracheal administration (Brattsand and Axelsson, 1997). However, some studies give evidence that a portion of the budesonide dose is retained in lung tissue longer than other steroids because it forms conjugates with long-chain fatty acids (mostly oleic acid) within cells (Tunek et al., 1997). Such conjugation does not appear to occur with beclomethasone dipropionate, fluticasone propionate or other inhaled glucocorticoids. Budesonide fatty acid conjugates act as an intracellular store of inactive drug since only free budesonide binds to the glucocorticoid receptor. Currently, this depot effect has not been directly correlated to an increase in the therapeutic effect.

4.8 Fluticasone Propionate (FP)

FP is commercially available as Flovent MDI (Glaxo-Wellcome) and the Diskhaler DPI (Glaxo-Wellcome). Doses of 100–200 mcg/day for children, 200–500 mcg/day for adults with mild asthma, 500–1000 mcg/day for adults with moderate asthma, and 1000–2000 mcg/day for adults with severe asthma are recommended (Meibohm et at, 1998). Following inhalation, 26% of the dose from MDI or 15% of the dose from DPI is deposited in the lung (Möllmann et at, 1998), while the majority impacts on the oropharyngeal region and is swallowed. Fluticasone propionate undergoes extensive first-pass metabolism, resulting in an oral bioavailability of less than 1%, and an overall bioavailability after inhalation of 10–15% (Falcoz et al., 1996a; Andersson et al., 1993). Absorption of the lipophilic fluticasone molecule is slow (MAT of 4.9 hours), leading to prolonged retention in the lungs and lower peak plasma concentrations (Derendorf, 1997).

Fluticasone propionate has a high RBA of 1800 and a high plasma protein binding of 90% (Meibohm, 1998) compared to TA and BUD. The volume of distribution of fluticasone propionate at steady state ($Vd_{55}$) is 318 L. which is in agreement with the high lipophilicity of the molecule (Mackie et al. 1996). Rapid hepatic clearance of 66 L/hr minimizes systemic side effects, with almost 87–100% of the drug excreted in the feces, and 340% as the inactive 17-carboxylic acid (Holliday et al., 1994).

After IV administration. FP follows a three-compartment body model with its terminal half-life ranging between 7.7–8.3 hours (Mackie et al. 1996). Absorption of FP in humans is slower than that of TA and BUD and is the overall rate-limiting step in the lungs, and as a result terminal half-life values of 10 hours have been reported after inhalation (Thorsson et al. 1997). In a recent study it was shown that the $t_{1/2}$ is dose-dependent and ranged between 5.2–7.4 hours with a mean of 6.0±0.7 hours (Möllmann et al., 1998). The reported value for the mean residence time of FP after inhaled administration, calculated as the area under the first moment curve (AUMC) divided by AUC, averaged 9.1±1.1 hours (ranging from 7.8–11 hours (Möllmann et al., 1998) ). The mean absorption time after inhalation of FP was found to range from 3.6–6.8 hours with a mean of approximately 5.0 hours (Möllmann et al., 1998).

4.9 Formulation Dependent Factors

Delivery devices such as dry powder inhalers and metered dose inhalers have been improved in the last few years such that pulmonary deposition can range from 10% for conventional delivery systems to up to 40% for recently developed third generation devices (Newman et al., 1997). As a general rule, pulmonary delivery devices with high pulmonary deposition are beneficial for achieving pulmonary targeting; however, efficient delivery is not as important for substances with low oral bioavailability, because systemic side effects related to orally absorbed drug are insignificant (Hochhaus et al., 1997).

PD/PD simulations were also able to demonstrate that pulmonary targeting depends on the dose. At low doses, pulmonary and systemic receptors are hardly occupied with small differences between pulmonary and systemic receptors. Pulmonary receptors are getting saturated at higher doses, while systemic levels are still too low to show significant receptor binding. At a certain point, a further increase in dose will not result in a further increase in receptor occupancy. However, more drug will enter the systemic circulation, resulting in an increase in the systemic receptor occupancy and a loss of pulmonary targeting. Thus, both low and high doses of a glucocorticoid will result in close superimposition of lung and liver receptor occupancy and, consequently, in low pulmonary targeting. These simulations suggest that there is a dose optimum for which maximum pulmonary selectivity is observed. Although it is recognized that a dose optimum might not necessarily be directly indicative of clinical response in asthma of varying severity, these relationships clearly show that overdosing and under-dosing will always go parallel with a decreased pulmonary targeting.

Interestingly, one of the predominant factors responsible for pulmonary targeting, the pulmonary mean residence time, has not been extensively evaluated. Pulmonary residence time is determined by the release rate of the inhaled particle from an inhaled solid (powder) or an alternative delivery system such as liposomes, the absorption rate of dissolved drug across pulmonary membranes and the mucociliary clearance which is able to remove drug particles from the upper portions of the lung. The absorption across membranes is a rapid process for lipophilic glucocorticoids (Burton and Schanker, 1974), and, consequently, the dissolution rate of a glucocorticoid powder will be the main determinant for controlling the pulmonary residence time. Simulations using a recently developed PD/PD model showed that for inhalation products with very rapid release kinetics—a solution would represent this extreme—no targeting is observed because of the very fast absorption from the lung into the systemic—circulation. With decreasing release rate (dissolution rate), pulmonary targeting is increased, as indicated by a dissociation of pulmonary and systemic receptor occupancies. A further decrease in release rate will consequently lead to a decrease in pulmonary targeting as a significant portion of the drug is removed via the mucociliary clearance and after swallowing is available for oral absorption. Thus, inhaled glucocorticoids should possess certain dissolution or release characteristics in order to show significant targeting.

4.10 Controlled Release

It has been demonstrated that encapsulation of glucocorticoids into liposomes can lead to the enhancement of therapeutic efficacy, with a reduction in their toxicity and prolongation of their therapeutic effect (Brattsand and Axelsson, 1997; Suarez et al., 1998). Other methods of obtaining controlled release in the lungs, such as polymeric microspheres and microencapsulation techniques (Zeng et al., 1995), are described in this section.

4.11 Biodegradable Microspheres

Biodegradable polymers are being used in a large number of biomedical applications such as resorbable sutures, internal fixation devices, degradable scaffolds for tissue regeneration, and matrices for drug delivery. The biocompatibility of these polymers has been reviewed (Therin et al., 1992). A variety of synthetic and natural polymers have been found to exhibit minimal inflammatory response in various implantation sites (Zeng et al., 1995).

The advantages of microspheres over liposomes include greater range of sizes, higher stability and shelf life, and longer retention in vivo (up to 6 months) (Zeng et al. 1995). Biodegradation is associated with materials that can be broken down by natural means such as enzymatic or hydrolytic degradation (Chu et al. 1995). Biodegradation of poly (lactic acid) (PLA), poly(glycolic acid) (PGA), and their copolymers poly(lactic-co-glycolic acid) (PLGA) yield the natural metabolic products lactic acid and glycolic acid, which are incorporated into the tricarboxiylic acid cycle and excreted (Edwards et al., 1997).

Although several reports of inhaled microsphere preparations have shown improvements in targeted and sustained drug release, there have been no reports on glucocorticoid microspheres. PLGA microspheres of isoproterenol, a beta-agonist bronchodilator, intratracheally administered in rats was shown to ameliorate bronchconstriction for 12 hours in contrast to 30 min after free isopreternol administration (Lai et al., 1993). Preparations of large, porous particles of PLGA encapsulated testosterone and insulin by double-emulsion solvent evaporation showed effects up to 96 hours while improving deposition (Edwards et al., 1997). Sustained release of 2% rifampicin from PLGA microspheres from 3–7 days in guinea pigs has been shown to reduce mycobacterium infection in macrophages (Hickey et al., 1998). Unfortunately, low encapsulation efficiencies (<40%) and concerns of accumulation of slowly degrading polymers in the lungs for long-term use have limited the therapeutic application of polymeric pulmonary sustained release systems.

4.12 Microencapsulation

The area of microencapsulation is relatively new, previously limited to solvent evaporation techniques (Thies, 1982; Manekar et al., 1992; Conti et al., 1992; Gopferich et al., 1994). Currently there are several different ways of applying coatings to particles in industry, mainly through spray-coating technologies (Gopferich et al., 1994). Pranlukast, a luekotriene inhibitor, encapsulated with hydroxypropylmethylcellulose (HPMC) nanospheres prepared by spray drying showed an improvement in inhalation efficiency but did not show a significant difference in the dissolution rate (Kawashima et al., 1998). The disadvantages of applying micron-thick coatings for sustained-release (10–100 microns thick) (Glatt, 1998) is that large quantities of solvents must be dried under strong venting and that an increase in particle size reduces the inhalation efficiency (Zeng et al., 1995; Talton, 1999).

5.0 EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Currently, dry powder inhalers (DPIs) are used to deliver various drugs to the lungs for localized or systemic delivery. Although current formulations and delivery systems are adequate for pulmonary drug therapy, they are limited by potential problems with pulmonary deposition characteristics as well as the residence time of the drug after inhalation (Hochhaus et al., 1997). Previously, liposomes were used as a model sustained release system with a substantial improvement in pulmonary targeting in rats (Suarez et al., 1998). Liposomes and microspheres have been investigated as sustained release delivery systems for the lung (Zeng et al., 1995; Edwards et al., 1997), but because of complicated manufacturing and wet processing, a novel dry coating technique previously developed for engineered particulates using pulsed laser deposition (PLD) is proposed (Fitz-Gerald, 1998). It is proposed that modification of the release rate of the drug from dry powders by applying a biodegradable polymer coating would greatly enhance the pulmonary residence time, and thus improve pulmonary targeting.

Over the past few years, the pulsed laser deposition (PLD) technique has emerged as one of the simplest and most versatile methods for the deposition of thin films of a wide variety of materials (Chrisey and Hubler, 1994). The stoichiometric removal of the constituent species from the target during ablation (i.e., a monomer and nanoclusters of polymer) from a polymer target, as well as the relatively small number of control parameters, are the two major advantages of PLD over some of the other physical vapor deposition techniques. No studies have currently been performed using biodegradable polymers for coating materials by PLD, so comparison of the molecular structure of the deposited films to original material was performed to ensure that the polymer structure remained intact after deposition.

Overall this section describes the use of PLD to ablate a target of biodegradable polymer, poly(lactic-co-glycolic acid) (PLGA 50:50), to coat budesonide (BUD) micronized drug particles for 10 (BUD10) and 25 (BUD25) min runs. Characterization of films deposited on silicon wafers or glass slides was performed using SEM. FTIR, and NMR to characterize polymer structure and morphology. The BUD10 and BUD25 coated powders were tested in vitro to assess differences in the dissolution rates. The BUD25 coated drug formulation was administered intratracheally in vivo in rats to monitor plasma concentration and improvement in pulmonary targeting. Comparison of the plasma concentrations after IT administration of the coated powders with uncoated BUD powders and IV administration of BUD solution, as well as with FP after IT administration, were performed to compare absorption rates. Finally, the pulmonary targeting of coating BUD25 powders after IT administration was compared with the pulmonary targeting of uncoated BUD and FP powders after IT administration and BUD solution after IV administration. Verification of deposited polymer on silicon wafers using NMR and FTIR was used to characterize molecular structure. The use of a coated particle formulation of budesonide (BUD25) with slower dissolution characteristics in vitro was delivered in vivo in rats to observe differences in absorption and pulmonary targeting.

Although the comparison of particle size and morphology using SEM was more or less qualitative and not quantitative, SEM photomicrographs of the polymeric coatings after deposition show the relatively nanometer thick level of coatings formed using the PLD technique. SEM photomicrographs of polymer deposited onto silicon wafers at different run times suggested that 100-nanometer size or smaller droplets were deposited and formed a continuous coating after several min. SEM photomicrographs comparing uncoated particles to coated particles showed no observable difference in particle size after coating, but this is difficult to quantitate with standard techniques at the nanometer level. Further analysis should be performed to accurately quantitate the coating structure and thickness, but HPLC analysis of dissolved coated powders in solution compared to pure powder showed polymer mass less than 0.1% weight.

Analysis of the polymer samples using FTIR and NMR verified that the deposited polymer retained its molecular structure after deposition. Analysis using FTIR was successful in confirming that the general composition peaks of the polymer backbone did not change dramatically after deposition. Characterization using NMR also showed similar characteristic 30 peaks between PLGA deposited on silicon wafers and original PLGA. Both techniques were not quantitative, though, because the sensitivity and the scans are dependent on the amount of material used, and as stated above only a small amount of polymer is deposited using this technique.

Dissolution analysis in vitro of BUD10 (10 min coating) and BUD25 (25 min coating) showed biphasic dissolution rates with $T_{50\%}$, of 29 and 60 min. respectively. There appears to be an early release of uncoated drug in the first 5 min. and then a slow release of drug from coated particles over 1–2 hours. This release may be beneficial to obtain therapeutic levels immediately, while the coated portion released over 1–2 hours maintains concentrations close to therapeutic levels longer while reducing systemic spillover.

In rat studies, the peak plasma concentration of BUD25 after intratracheal administration was at 1.0 hour (vs. 0.5 hour for free powders). While the AUC appears to be higher than for the free BUD powders, verification of powder formulations showed an approximately two-fold increase in the dose administered to rats. The MAT was calculated to be 0.8 hour vs. 0.3 hour for the free powder, interestingly similar to the in vitro dissolution half-life of 1.0 hour. Although this change in the in vitro dissolution and in vivo absorption rate was an improvement, further studies should be performed with coatings of longer dissolution rate to further evaluate the relationship of dissolution rate on absorption rate and pulmonary targeting.

The receptor-binding profiles in rats for BUD25 showed an improvement in pulmonary targeting over BUD free powders in the lung vs. liver and lung vs. kidney, and a higher pulmonary targeting than FP when comparing the receptor binding profiles in the lung vs. kidney. In addition, the pulmonary MET increased almost 2 hours to 5.5 hours compared to 3.6 hours after the free powder. Considering the improvement in pulmonary targeting by only changing the dissolution rate of budesonide, this strongly suggests that the increase in pulmonary targeting of BUD25 coated powders is obtained by controlling the release rate of budesonide into the lung.

Currently, there is much interest in controlling release of biotechnology and gene therapy agents in the lungs (Edwards et al., 1997). Other techniques including low-density microspheres (Edwards et al. 1997), spray-coated microparticles (Witschi and Mrsny, 1999), conventional microspheres (Pillai et al., 1998), and liposomes (Brattsand and Axelsson, 1997; Suarez et al., 1998) have been researched but currently have not been granted Food and Drug Administration approval. Increases in the pulmonary half-lives up to 18 hours of locally-active agents in liposome formulations have been shown (Fielding and Abra, 1992; McCullough and Juliano, 1979). In particular, the plasma concentration profiles and pulmonary targeting of liposome encapsulated triamcinolone acetonide phosphate showed an increase in the mean absorption time from liposomal release (5.6 hours) and resulted in a statistically significant increase in pulmonary targeting (Suarez et al., 1998). Although the PLGA coated budesonide dry powders presented here only resulted in an increase in the MAT of 0.8 hour when compared to uncoated budesonide, a statistically significant increase in pulmonary targeting was also observed. This would indicate that small changes in the release rate of pulmonary drug formulations enhance the local vs. systemic effects observed (Talton, 1999).

5.2 Example 2

Figure 6:
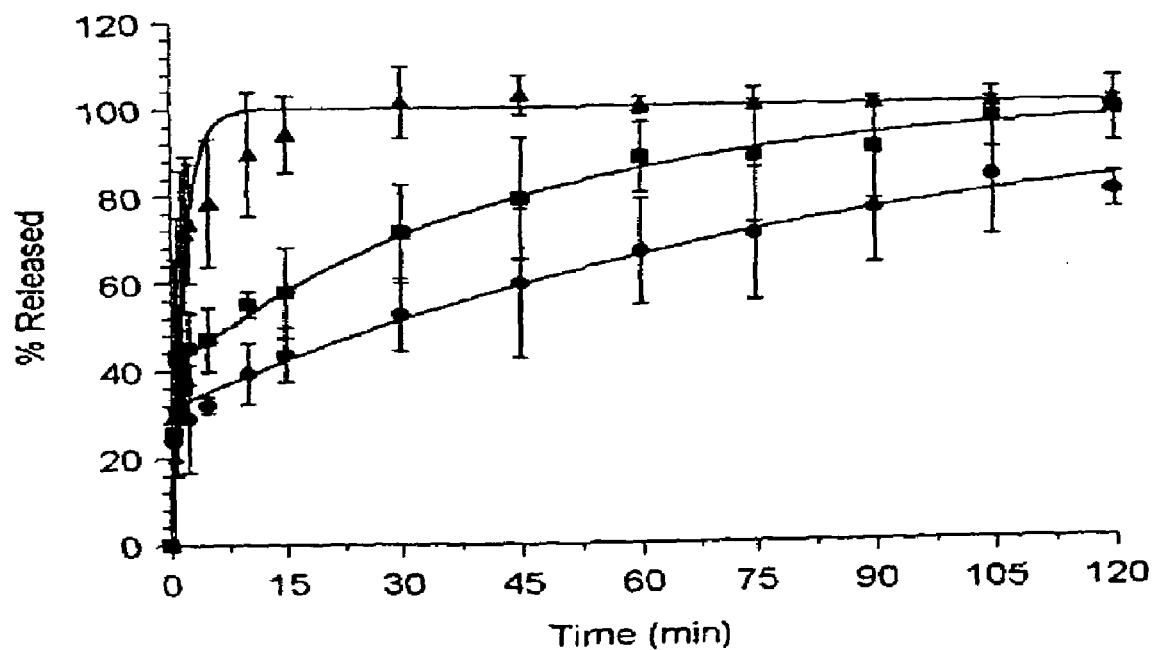

Various coatings of poly(lactic-glycolic) acid (PLGA) were deposited onto mironized TA particles, another currently used anti-asthma drug, under similar coating conditions with PLGA, in order to test sustained-release dissolution profiles. The coatings were of nanometer 10 dimensions and extended release rate of the drug beyond 24 hours, as shown in FIG. 6.

Figure 7:
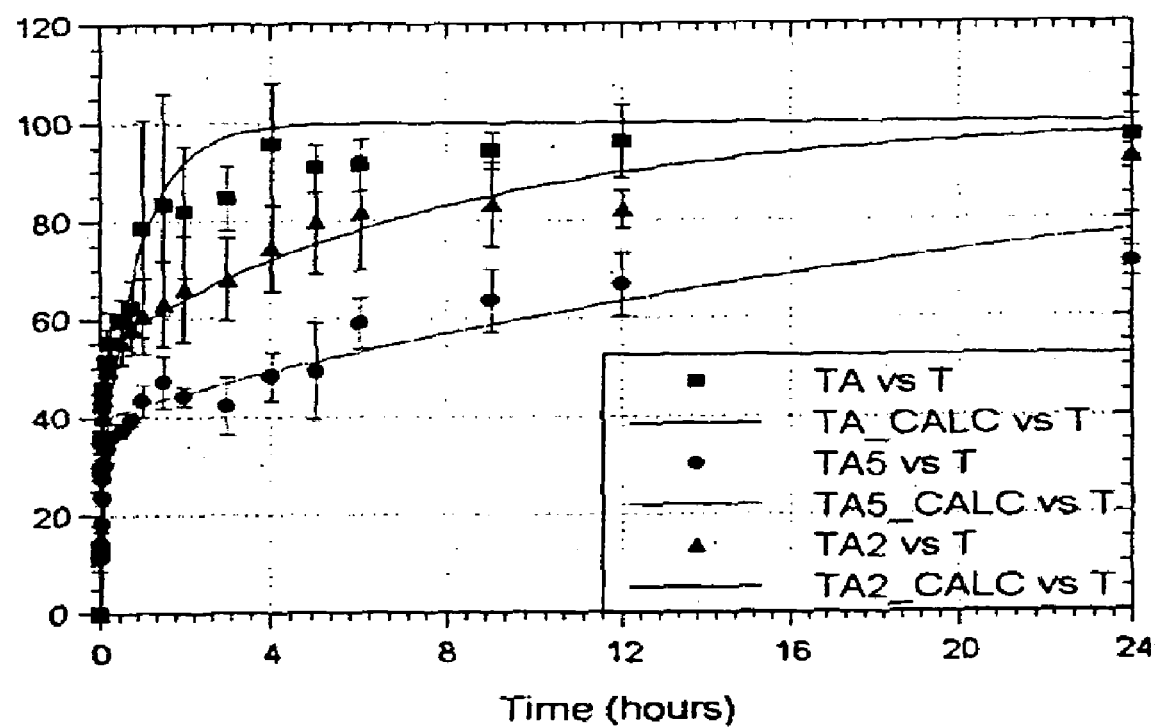

The coated TA2 powder (coated at 2 hertz) reached 90% release at approximately 12 hours and the coated TA5 powder (coated at 5 hertz) reached 90% release beyond 24 hours. This was compared to uncoated micronized TA that reached 90% release at approximately 2 hours (FIG. 7).

Aerodynamic particle size of coated powders, using an Anderson Mark II Cascade Impactor, showed no statistically significant increase in particle size. In addition, although not statistically significant, the respirable fraction (stages 3 to 5) of coated TA showed an increased deposition compared to uncoated TA.

In vitro rat alveolar cell survival and proliferation at various concentrations of coated vs. uncoated drugs was compared using the tetrazolium based colorimetric assay (MTT). Cell viability decreased when incubating cells with high concentration for a longer time period, with no significant difference in cell toxicity between uncoated and coated TA.

5.3 Example 3

*Mycobacterium tuberculosis* (MTB) is the most prevalent infectious agent infecting one third of the world's population. Coinfection of tuberculosis (TB) and Human Immunodeficiency Virus (HIV) is present in a significant number of new TB cases. Particularly dangerous is the emergence of Multiple Drug Resistant (MDR) strains that increase the spread and chances of infection of this airborne microorganism. Therefore, the need exists for 30 developing drugs and pharmaceutical formulations that are more effective in localized treatment of the disease. This example describes the preparation of microencpsulated drug particles containing rifampicin, and their delivery to the lungs to specifically target alveolar macrophages, the host cells of this organism.

MTB bacilli are generally inhaled enter the alveolar macrophages via specific binding followed by internalization (Fenton, 1996). From the lungs the microorganism is transmitted to other organs through the blood supply, but the primary site of infection and highest concentration of infected cells remains the lungs. Generally, oral therapy of 450–600 mg a day of rifampicin is the first line therapy for tuberculosis. Unlike in the treatment of asthma, currently there are no inhaled formulations for TB therapy, but microsphere preparations have been investigated and shown efficacy in guinea pigs (Hickey, 1998). In addition, it has been shown that sustained-release of inhaled glucocorticoids in asthma therapies, such as triamcinolone acetonide and budesonide, showed improved local vs. systemic effects. While inhalation therapy is used to induce significant pulmonary effects with reduced systemic side effects, there are a number of factors that need to be considered for optimized pulmonary targeting. These include low oral bioavailability, high systemic clearance, and distinct pulmonary deposition (Hochhaus, 1997). The most important factor that has been neglected in the literature is the slow pulmonary absorption of the deposited drug. The particle size of commercially available rifampicin ranges from about 100 to about 500 microns. Using a milling process that comprises jets of air in a small chamber disrupting the drug (basically by the particles hitting each other and breaking apart) the inventors prepared particles having an average diameter of about 1 to about 5 microns. About 25% of the particles were above 5 microns, about 50% were in the range of from about 1 to about 5 microns, and 25% of the particles were smaller than about 1 micron. These ratios can be altered by controlling the runtime and pressure of the jets in the mill.

Figure 8:
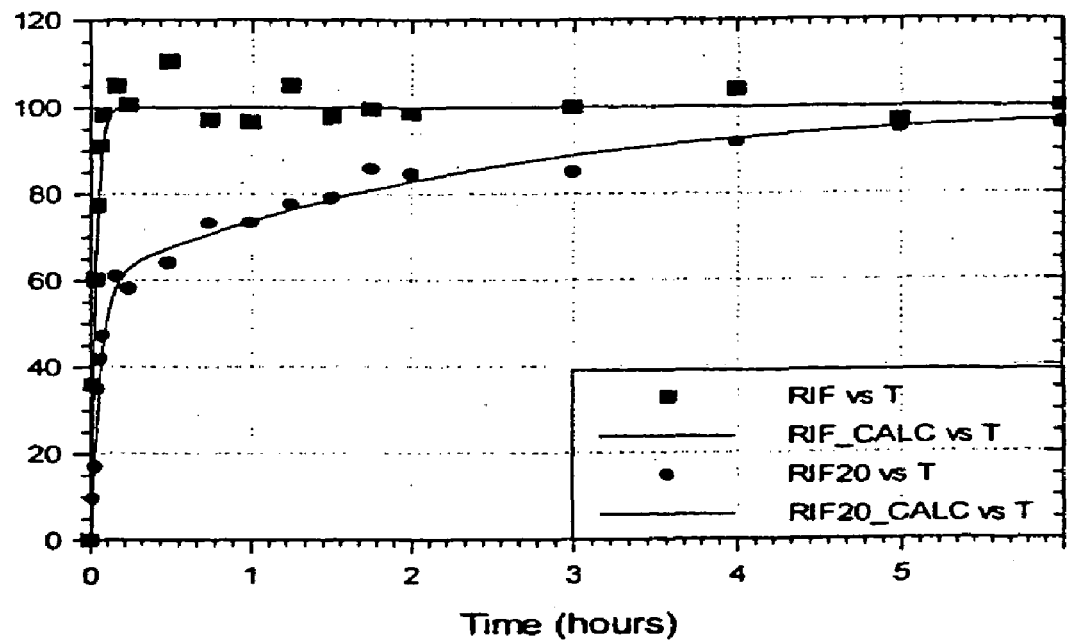

500 mg of the the 1 to 5 micron size fraction was selected and coated for 10 minutes using the laser ablation method described above. In vitro dissolution of coated rifampicin reached 90% release after 6 hours compared to fast release of uncoated RIF, which reached 90% release within 15 min (FIG. 8). Similar to TA, particle size did not increase significantly after coating and showed no difference in cell viability after incubation compared to uncoated powders at similar concentrations.

6.0 REFERENCES

The following literature citations as well as those cited above are incorporated in pertinent part by reference herein for the reasons cited in the above text:

Adjei and Garren. "Pulmonary delivery of peptide drugs: effect of particle size on bioavailability of leuprolide acetate in healthy male volunteers," *Pharm. Res.*, 7(6): 565–69, 1990.

Adkins, J. C. and D. McTavish. "Salmeterol. A review of its pharmacological properties and clinical efficacy in the management of children with asthma." *Drugs* 54(2): 331–54, 1997.

Agertoft and Pedersen. "Importance of the inhalation device on the effect of budesonide," *Arch. Dis. Child,* 69(1): 130–33, 1993.

Agertoft and Pedersen. "Influence of spacer device on drug delivery to young children with asthma," *Arch. Dis. Child,* 71(3):217–19, 1994.

Ahrens, Lux, Bahl and Han, "Choosing the metered-dose inhaler spacer or holding chamber that matches the patient's need: evidence that the specific drug being delivered is an important consideration," *J. Allergy Clin. Immunol.,* 96(2):288–94, 1995.

Allera and Wildt, "Glucocorticoid-recognizing and -effector sites in rat liver plasma membrane. Kinetics of corticosterone uptake by isolated membrane vesicles-II. Comparative influx and efflux," *J. Steroid Biochem. Mol. Biol.,* 42(7):757–71, 1992.

Andersson, Brattsand, Dahlström and Edsbaecker, "Oral availability of fluticasone propionate," *Br. J. Clin. Pharmac.,* 36:135–36, 1993.

Astra-USA, "Budesonide Inhalation powder: 200 and 400 mg/dose (Pulmicort Turbohaler) NDA20–441," *Clin. Pharmacol. Biopharm. Rev.,* 1–51, 1997.

Bamberger. Bamberger, de Castro and Chrousos, "Glucocorticoid receptor beta, a potential endogenous inhibitor of glucocorticoid action in humans," *J. Clin. Invest.,* 95(6):2435–41, 1995.

Barnes and Pedersen, "Efficacy and safety of inhaled corticosteroids in asthma," *Am. Rev. Respir. Dis.,* 148:S1–S26, 1993.

Barnes et al., "Worldwide clinical experience with the first marketed leukotriene receptor antagonist," *Chest,* 111(2 Suppl):52S–60S, 1997.

Barnes, "Asthma: New therapeutic approaches," *Br. Med. Bull.* 48(1):231–47, 1992.

Barnes. "Inhaled glucocorticoids for asthma." *N. Engl. J. Med.,* 332:868–75, 1995.

Barnes. "Inhaled glucocorticoids: new developments relevant to updating of the asthma management guidelines." *Respir. Med,* 90(7):379–84, 1996.

Barnes. "Molecular mechanism of steroid action in asthma." *J. Allergy Clin. Immunol.* 97:159–68, 1996.

Barnes. "Molecular mechanisms of antiasthma therapy," *Ann. Med.* 27(5):531–35, 1995.

Barnes, "New concepts in the pathogenesis of bronchial hyperresponsiveness and asthma," *J. Allergy Clin. Immunol.* 86(6):1013–26, 1989a.

Barnes. "Our changing understanding of asthma," *Resp. Med.* 83:517–23, 1989b.

Barry, "The effect of delay multiple actuations and spacer static change on the in vitro delivery of budesonide from the Nebuhaler," *Br. J. Clin. Pharmacol.* 40(1):76–78, 1995.

Baxter, Rousseau, Higgins and Tomkins. "Mechanism of glucocorticoid hormone action and of regulation of gene expression in cultured mammalian cells," in "The Biochemistry of Gene Expression in Higher Organism," Pollack and Wilson Lee (eds.), Australian New Zealand Book, Sidney, pp. 206–24, 1973.

Beato, Rousseau and Feigelson. "Correlation between glucocorticoid binding to specific liver cytosol receptors and enzyme induction," *Biochem. Biophys. Res. Commun,* 47:1464–72, 1972.

Becker and Grass, "Suppression of phagocytosis by dexamethasone in macrophage culture: Inability of arachidonic acid, indomethacin, and nordihydroaiaretic acid to reverse the inhibitory response mediated by a steroid-inducible factor," *Int. J. Immunopharmac.,* 7:83947, 1985.

Blaiss, "New pharmacologic agents in the treatment of asthma," *Allergy Proc.,* 14(1):17–21, 1993.

Blanchet, Fincher, Jackson, Shah and Gardner, "Laser ablation and the production of polymer films," *Science,* 262: 719–21, 1993.

Bloemena, Weinreich and Schellekens, "The influence of prednisolone on the recirculation of peripheral blood lymphocytes in vivo," *Clin. Exp. Imm.* 80:460–66, 1990.

Borgström and Nilsson, "A method for determination of the absolute pulmonary bioavailability of inhaled drugs: Terbutaline," *Pharm. Res.,* 7(10): 1068–70, 1990.

Braat, Oosterhuis, Koopmans, Meewis and VanBoxtel, "Kinetic-dynamic modeling of lymphocytopenia induced by the combined action of dexamethasone and hydrocortisone in humans, after inhalation and intravenous administration of dexamethasone." *Journal of Pharmacology and Experimental Therapeutics.* 262(2):509–15, 1992.

Brain and Valberg, "Deposition of aerosol in the respiratory tract," *Am. Rev. Respir. Dis.,* 120(6):1325–73, 1979.

Brattsand and Axelsson. "Basis of ainvav selectivity of inhaled glucocorticoids," in "Inhaled glucocorticoids in asthma." Scheimer. Busse and O'Byme (eds.), Marcel Dekker, New York, pp. 351–79, 1997.

Brattsand and Seiroos, "Current drugs for respiratory diseases." in "Drugs and the Lung," Page and Metzger (eds.), Raven Press, New York, pp. 42–110, 1994.

Brattsand, Thalen, Roempke, Kaellström and Gruvstad. "Influence of 16a, 17a-acetal substitution and steroid nucleus fluorination on the topical to systemic ratio of glucocorticoid," *J. Steroid Biochem.*, 16:779–86, 1982.

Brogden and McTavish, "Budesonide. An updated review of its pharmacological properties, and therapeutic efficacy in asthma and rhinitis," [published errata appear in Drugs, 44(6):1012, 1992 and 45(1):130, 1993], *Drugs*, 44:375–407, 1992.

Brogden, Heel, Speight and Avery, "Beclomethasone dipropionate. A reappraisal of its pharmacodynamic properties and therapeutic efficacy after a decade of use in asthma and rhinitis," *Drugs*, 28(2):99–126, 1984.

Brown and Schanker, "Absorption of aerosolized drugs from the rat lung," *Drug Metab. Dispos.*, 11(4):355–60, 1983.

Burton and Schanker, "Absorption of corticosteroids from the rat lung," *Steroids*, 23(5):617–24, 1974.

Burton and Schanker, *Steroids*, 23:617–24, 1974.

Byron et al., "Aerosol electrostatics, 1: Properties of fine powders before and after aerosolization by dry powder inhalers," *Pharm Res.*, 14(6):698–705, 1997.

Byron, "Prediction of drug residence times in regions of the human respiratory tract following aerosol inhalation," *J. Pharm. Sci.*, 75:433–38, 1986.

Caesaret et al., "Treatment of active Crohn's ileocolitis with oral pH-modified budesonide, Germany Budesonide Study Group," *Z. Gastroenterol.*, 33(5):247–50, 1995.

Chanoine, Grenot, Heidmann and Junien, "Pharmacokinetics of butixcort 21-propionate, budesonide, and beclomethasone diporopionate in the rat after intratracheal, intravenous, and oral treatments," *Drug Metab. Dispos.*, 19(2):546–53, 1991.

Chaplin, Cooper, Segre, Oren, Jones and Nerenberg, "Correlation of flunisolide plasma levels to eosinopenic response to humans," *J. Allergy Clin. Immunol.*, 65:445–53, 1980b.

Chaplin, Rooks, Swenson, Cooper, Nerenberg and Chu "Flunisolide metabolism and dynamics of a metabolite." *Clin. Pharmacol. Ther.* 27:402–13, 1980a.

Chrisey and Hubler. "Pulsed Laser Deposition of Thin Films." 1:200, 1994.

Chu, Monosov and Amiel. "In situ assessment of cell viability within biodegradable polylactic acid polymer matrices." *Biomaterials.* 16(18): 1381–84, 1995.

Conti, Pavanetto and Genta, "Use of polylactic acid for the preparation of microparticulate drug delivery systems," *J. Microencapsul.*, 9(2):153–66, 1992.

Dahlberg, Thalen, Brattsand, Gustafsson, Johansson, Roemke and Saartrok. "Correlation between chemical structure, receptor binding, and biological activity of some novel, highly active 16a, 17a acetal substituted glucocorticoids," *Mol. Pharmacol.*, 25:70–78, 1984.

Dahlen et al., "Effect of the leukotriene receptor antagonist MK-0679 on baseline pulmonary function in aspirin sensitive asthmatic subjects [see comrnents]," *Thorax*, 48(12):1205–10, 1993.

Davies and Morris, "Physiological parameters in laboratory animals and humans [editorial]," *Pharm. Res.*, 10(7):1093–95, 1993.

Demoly, Jaffuel, Sahla, Bousquet, Michel and Godard, "The use of home nebulizers in adult asthma." *Respir. Med*, 92(4):624–27, 1998.

Derendorf and Moellmann, "Pharmacodynamics of methylprednisolone after single intravenous administration to healthy volunteers," *Pharm. Res.*, 8:263–68, 1991.

Derendorf, "Phammacokinetic and pharmacodynamic properties of inhaled corticosteroids in relation to efficacy and safety," *Respir. Med*, 91 Suppl. A:22–28, 1997.

Derendorf, Hochhaus, Meibohm, Möllmann and Barth, "Pharmacokinetics and pharmaco-dynamics of inhaled corticosteroids," *J. Allergy Clin. Immunol.*, 101(4 Pt 2):S440–46, 1998.

Derendorf, Hochhaus, Möllmann, Barth, Krieg, Tunn and Möllmann, "Receptor-based pharmacokinetic/pharmacodynamic analysis of corticosteroids," *J. Clin. Pharmacol.*, 33(2):115–23, 1993.

Derendorf, Hochhaus, Rohatagi, Möllmann, Barth and Erdmann, "Oral and pulmonary bioavailability of triarncinolone acetonide," *J. Clin. Pharmacol.*, 35:302–05, 1995.

Derendorf, Moellmann, Barth, Moellmann, Tunn and Krieg, "Pharmacokinetics and oral bioavailability of hydrocortisone," *J. Clin. Pharmacol.* 31:473–76, 1991.

Derendorf, Moellmann, Rohdewald, Rehder and Schmidt. "Kinetics of methylprednisolone and its hemisuccinate ester," *Clin. Pharmacol. Ther.*, 37:502–07, 1985.

Derendorf, Möllmann, Hochhaus, Meibohm and Barth. "Clinical PK/PD modeling as a tool in drug development of corticosteroids." *Int. J. Clin. Pharmacol. Ther.*, 35:481–38, 1997.

Devadason et al., "Lung deposition from the Turbuhaler in children with cystic fibrosis." *Eur. Respir. J.*, 10(9):2023–8, 1997.

Devadason, Everard, MacEarlan, Roller, Summers, Swift, Borgström and Le Souef "Lung deposition from the Turbuhaler in children with cystic fibrosis," *Eur. Respir. J.*, 10(9):2023–28, 1997.

Diamant, Eshiel and Ben-Or, "Interaction of cortisol with the neural retina of the chick embryo in culture." *Cell Differentiation*, 4:101–12, 1975.

Didonato, "Molecular mechanisms of immunosuppression and anti-inflammatory activities by glucocorticoids," *Am. J. Resp. Crit. Care Med.*, 154:S11–15, 1996.

Druzgala, Hochhaus and Bodor, "Soft drugs 10: Blanching activity and receptor binding affinity of a new type of glucocorticoid: Loteprediiol etabonate," *J. Ster. Biochem. Mol. Biol.*, 38(2):149–54, 1991.

Duggan, Yeh, Matalia, Ditzler and McMahon, "Bioavailability of oral dexamethasone," *Clin. Pharmacol. Ther.*, 18(2):205–09, 1975.

D'Urzo, "Long-acting beta 2-agonists. Role in primary care asthma treatment," *Can Fam Physician*, 43:1773–7, 1997.

Eccles and Mygind, "Physiology of the upper airways in allergic disease," *Clin. Rev. Allergy*, 3(4):501–16, 1985.

Edsbaecker and Jendro, "Modes to achieve topical selectivity of inhaled glucocorticoids-focus on budesonide," in "Respiratory Drug Delivery VI," Dalby, Byron and Farr (eds.), Interpharm Press. Inc. Buffalo Grove, Ill., pp. 71–82, 1998.

Edsbaecker and Szefler, "Glucocorticoid pharmacokinetics—principles and clinical applications," in "Inhaled Glucocorticoids in Asthma," Schleimer, Busse and O'Byrne (eds.), Marcel Dekker, New York, pp. 381–446, 1997.

Edsbaecker, Andersson, Lindberg, Paulson, Ryrfeldt and Thalen, "Liver metabolism of budesonide in rat, mouse, and man," *Drug Met. Disp.*, 15(3):403–11, 1987.

Edwards et al. "Large porous particles for pulmonary drug delivery," *Science*, 276(5320):1868–71, 1997.

Esmailpour, Hogger, Rabe, Heitmann, Nakashima and Rohdewald, "Distribution of inhaled fluticasone propionate between human lung tissue and serum in vivo," *Eur. Respir. J.*, 10(7): 1496–99, 1997, Evans, "The steroid and thyroid hormone receptor superfamily." *Science*, 240–889–95, 1988.

Everard, M. L. S. G. Devadason. et al., "Particle size selection device for use with the Turbohaler." *Thorax*, 51(5):537–9, 1996.

Falcoz, Brindley, Mackie and Bye, "Input Rate into the systemic Circulation of fluticasone propionate after a 1000 μg inhaled dose from the diskhaler," *J. Clin. Pharmacol.*, 35:927, 1996b.

Falcoz, Mackie, McDowall, McRae, Yogendran, Ventresca and Bye, "Oral bioavailability of fluticasone propionate in healthy subjects," *Brit. J. Clin. Pharmacol.*, 41:459P≠60P, 1996a.

Farr, Kellaway, et al., "Comparison of solute partitioning and efflux of liposomes formed by a conventional and aerosolized method," *Int. J. Pharmaceut.*, 51:3946, 1989.

Farr, Kellaway, Parry-Jones and Woolfrey, "Technetium as a marker of liposomal deposition and clearance in the human lung," *Intern. Symp. Control. Rel. Bioact. Mater.*, 12:219–20, 1985.

Farr, Rowe, Rubsamen and Taylor, "Aerosol deposition in the human lung following administration from a microprocessor controlled pressurized metered dose inhaler, "*Thorax*, 50(6):639–44, 1995.

FDA, "SUPAC-MR: Modified Release Solid Oral Dosage Forms Guidelines," Food and Drug Administration, Washington, D.C., 1998.

Fenton and Vermeulen, "Immunopathology of tuberculosis: roles of macrophages and monocytes," *Infect. Immun.*, 64(3):683–90, 1996.

Fielding and Abra, "Factors affecting the release rate of terbutaline from liposome formulations after intratracheal instillation in the guinea pig," *Pharm. Res.*, 9(2):220–23, 1992.

Fielding and Abra, *Pharm. Res.*, 9:220–23, 1992.

Fitz-Gerald, "Synthesis and Characterization of Engineered Particulates with Controlled Surface Architecture," *PhD Dissertation, University of Florida*, 1998.

Fredorak et al., "Budenoside-beta-D-glucuronide: A Potential Prodrug for Treatment of Ulcerative Colitis." *Journal of Pharmaceutical Sciences*, 84(6):677–681, 1995.

Ganderton, "General factors influencing drug delivery to the lung," *Respir. Med.*, 91 Suppl A:13–16, 1997.

Gibaldi and Perrier, "Pharmacokinetics." $2^{nd}$ ed., Marcel Dekker, New York, 1982.

Glatt, "Multi-purpose Fluid Bed Processing," *Product Literature*, 1998.

Glaxo-Wellcome, "FLOVENT Product Information." Research Triangle Park, N.C., 1996.

Gonda, "A semi-empirical model of aerosol deposition in the human respiratory tract for mouth inhalation." *J. Pharm. Pharmacol.*, 33(11):692–96, 1981.

Gonda, "Drugs administered directly into the respiratory tract: Modeling of the duration of effective drug levels." *J. Pharm. Sci.*, 77:340–46, 1988.

Gonzalez-Rothi, Suarez, Hochhaus, Schreier, Lukyanov, Derendorf and Dalla Costa, "Pulmonary targeting of liposomal triamcinolone acetonide phosphate." *Pharm. Res.*, 13:1699–703, 1996.

Gopferich, Alonso and Langer, "Development and characterization of microencapsulated microspheres," *Pharm. Res.*, 11(11): 1568–74, 1994.

Goundalkar and Mezei, "Chemical modification of triamcinolone acetonide to improve liposomal encapsulation," *J. Pharm. Sci.*, 73(6):834–35, 1983.

Grahnen, Eckernas, Brundin and Ling-Andersson, "An assessment of the systemic activity of single doses of inhaled fluticasone propionate in healthy volunteers," *Br. J. Clin. Pharmacol.*, 38:521–25, 1994.

Hansen and Robitaille, "Formation of polymer films by pulsed laser evaporation," *Applied Physics Letters*, 52(1): 81–83, 1988.

Harding, "The human pharmacology of fluticasone propionate," *Respir. Med*, 84:A25–A29, 1990.

Hardy, Newman and Knoch, "Lung deposition from four nebulizers," *Respir. Med*, 87(6):461–65, 1993, Harvey, O'Doherty, Page, Thomas, Nunan and Treacher, "Comparison of jet and ultrasonic nebulizer pulmonary aerosol deposition during mechanical ventilation," *Eur. Respir. J.*, 10(4):905–09, 1997.

Hickey et al., "Efficacy of rifampicin-poly(lactide-co-glycolide) microspheres in treating tuberculosis. In: Respiratory Drug Delivery VI, Hilton Head, SC: Interpharm Press. Inc., 1998.

Hickey, Suarez, Bhat, O'Hara, Lalor, Atkins, Hopfer and McMurray, "Efficacy of rifampicin-poly(lactide-co-glycolide) microspheres in treating tuberculosis," in "Respiratory Drug Delivery VI," Interpharm Press, Inc., Hilton Head. SC, 1998.

Hill and Slater, "A comparison of the performance of two modern multidose dry powder asthma inhalers." *Respir. Med*, 92(1):105–10, 1998.

Hindle, Newton and Chrystyn, "Relative bioavailability of salbutamol to the lung following inhalation by a metered dose inhaler and a dry powder inhaler (abstract)," *Thorax*, 48:433–34, 1993.

Hochhaus and Derendorf, "Dose optimization based on pharmacokinetic/pharmacodynamic modeling," in "Handbook of pharmacokinetic/pharmacodynamic correlation," Derendorf and Hochhaus (eds.), CRC, New York, pp. 79–120, 1995.

Hochhaus, "Binding affinities of commercially available glucocorticoids to the glucocorticoid receptor of the human lung," in "Institute of Pharmaceutical Chemistry," Westfaelische Wilheims Universitaet: Muenster, 1983.

Hochhaus, Derendorf, Möllmann and Gonzalez-Rothi, "Pharmacokinetic/pharmacodynamic Aspects of Aerosol Therapy Using Glucocorticoids as a Model," *J. Clin. Pharmacol.*, 37:881–92, 1997.

Hochhaus, Druzgala, Hochhaus, Huang and Bodor, "Glucocorticoid activity and structure activity relationships in a series of some novel 17 a-ether-substituted steroids: influence of 17a-substituents," *Drug Des. Del.*, 8:117–25, 1991.

Hochhaus, Gonzalez-Rothi, Lukyanov, Derendorf, Schreier and Dalla Costa, "Assessment of glucocorticoid lung targeting by ex-vivo receptor binding studies," *Pharm. Res.*, 12:134–37, 1995.

Hochhaus, Möllmann and Barth, "Glucocorticoids for intra-articular therapy: Pharmacodynamic characterization via receptor binding studies." *Akt. Rheumatol*, 15:66–69, 1990.

Hochhaus, Möllmann, Derendorf and Gonzalez-Rothi, "Pharmacokinetic/pharmacodynamic aspects of aerosol therapy using glucocorticoids as a model," *J. Clin. Pharmacol.*, 37:881–92, 1997.

Hochhaus, Rohdewald, Möllmann and Grechuchna, "Identification of glucocorticoid receptors in normal and neoplastic human lungs," *Resp. Exp. Med.*, 182:71–78, 1983.

Hochhaus, Suarez, Gonzales-Rothi and Schreier. "Pulmonary targeting of inhaled glucocorticoids: How is it influenced by formulation?," in "Respiratory Drug Delivery VI," Dalby, Byron and Farr (eds.), Interpharm Press, pp. 45–52, 1998.

Hoegger and Rohdewald, "Binding kinetics of fluticasone propionate to the human glucocorticoid receptor," *Steroids*, 59:597–602, 1994.

Hoegger and Rohdewald, "Glucocorticoid receptors and fluticasone propionate," *Rev. Cont. Pharmacother.*, 9(8): 501–19, 1998.

Holliday, Faulds and Sorkin, "Inhaled fluticasone propionate. A review of its pharmacodynamic and pharmacokinetic properties, and therapeutic use in asthma," *Drugs*, 47(2):318–31, 1994.

Hrkach, Peracchia, Domb, Lotan and Langer, "Nanotechnology for biomaterials engineering: structural characterization of amphiphilic polymeric nanoparticles by 1H NMR spectroscopy," *Biomaterials*, 18(1):27–30, 1997.

Huang, Tamada, Hochhaus and Bodor, "An AM 1-based model for the estimation of the relative binding affinity for glucocorticoids," in "$1^{st}$ Drug Optimization via Retrometabolism Conference," Amelia Island: Die Pharmazie, 1997.

Hunt, "Liposome Disposition in vivo: V. Liposome stability in plasma and implications for drug carrier function," *Biochim. Biophys. Acta*, 719:450–63, 1982.

Hunt, MacGregor and Siegel, *Pharm. Res.*, 3:333–44, 1986.

Johnson, "Pharmacodynamics and pharmacokinetics of inhaled glucocorticoids," *J. Allergy Clin. Immunol.*, 97:169–76, 1996.

Jonsson, Astrom and Andersson, "Budesonide is metabolized by cytochrome P450 3A (CYP31) enzymes in human liver," *Drug Metab. Dispos.*, 23(1):137–42, 1995.

Jusko, "Corticosteroid pharmacodynamics: Models for a broad array of receptor-mediated pharmacodynamic effects," *J. Clin. Pharmacol.*, 30:303–10, 1990.

Kamada, Szefler, Martin, Lazarus and Lemanske, "Issues in the use of inhaled glucocorticoids," *Am. J. Respir. Crit. Care Med.*, 153:1739–47, 1996.

Kawashima, Serigano, Hino, Yamamoto and Takeuchi, "A new powder design method to improve inhalation efficiency of pranlukast hydrate dry powder aerosols by surface modification with hydroxypropylmethylcellulose phthalate nanospheres," *Pharm. Res.*, 15(11):1748–52, 1998.

Kelly, "Comparison of inhaled corticosteroids," *Ann. Pharmacother.*, 32(2):220–32, 1998b.

Kelly, "Establishing a therapeutic index for the inhaled corticosteroids: Part I. Pharmaco-kinetic/pharmacodynamic comparison of the inhaled corticosteroids," *J. Allergy Clin. Immunol.*, 102(4 Pt 2):S36–51, 1998a.

Kreitz, Domm and Mathiowitz, "Controlled delivery of therapeutics from microporous membranes. II. In vitro degradation and release of heparin-loaded poly(D,L-lactide-co-glycolide)." *Biomaterials*. 18(24): 1645–51, 1997.

Krishnaswami, Mollmann, Derendorf and Hochhaus, "A sensitive APCI MRM LC/MS method for the quantification of fluticasone propionate in human plasma," *Pharm. Res., submitted.* 1999.

Lackner, Daufeldt, Wildt and Allera, "Glucocorticoid-recognizing and -effector sites in rat liver plasma membrane. Kinetics of corticosterone uptake by isolated membrane vesicles. III. Specificity and stereospecificity," *J. Steroid Biochem. Mol. Biol.*, 64(1–2):69–82, 1998.

Lai, Mehta, Thacker, Yoo, McNamara and DeLuca, "Sustained bronchodilation with isoproterenol poly(glucolide-co-lactide) microspheres." *Pharm. Res.*, 10(1):119–25, 1993.

Laitinen, Laitinen, Heino and Haahtela, "Eosinophilic airway inflammation during exacerbation of asthma and its treatment with inhaled corticosteroid," *Am. Rev. Respir. Dis.*, 143(2):423–27, 1991.

Leflein, Brown, Hill, Kelly, Loffert, Nelson and Szefler, "Delivery of glucocorticoids by jet nebulization: aerosol characteristics and output," *J. Allergy Clin. Immunol.*, 95(5 Pt 1):944–49, 1995.

Li, Arenholz, Heitz and Bauerle, "Pulsed-laser deposition of crystalline Teflon (PTFE) films," *App. Surf. Sci.*, 125: 17–22, 1998.

Li, Tattam, Brown and Seale, "Determination of epimers 22R and 22S of budesonide in human plasma by high-performance liquid chromatography-atmospheric pressure chemical ionization mass spectrometry," *J. Chromatogr. B. Biomed. Appl.*, 683(2):259–68, 1996.

Linn, F. V. and M. A. Peppercorn, "Drug therapy for inflammatory bowel disease: Part I." *Am J. Surg.*, 164(1): 85–9, 1992.

Lipworth and Clark, "Comparative lung delivery of salbutamol given via Turbuhaler and Diskus dry powder inhaler devices," *Eur. J. Clin. Pharmacol.*, 53(1):47–49, 1997.

Lipworth, "Clinical pharmacology of corticosteroids in bronchial asthma," *Pharmacol. Ther.*, 58(2):173–209, 1993.

Lipworth, B. J., "Pharmacokinetics of inhaled drugs [see comments]." *Br J Clin Pharmacol*, 42(6):697–705, 1996.

Liu and Regen, "Control over vesicle rupture and leakage by membrane packing and by the aggregation state of an attacking surfactant," *J. Am. Chem. Soc.*, 115:708–13, 1992.

Loennebo, Grahnen, Brundin, Ling-Andersson and Eckernas. "An assessment of the systemic effects of single and repeated doses of inhaled fluticasone proprionate and inhaled budesonide in healthy volunteers," *Eur. J. Clin. Pharmacol.* 49:459–63, 1996.

Loew, Schuster and Graul, "Dose-dependent pharmacokinetics of dexamethasone." *Eur. J. Clin. Pharmacol.* 30:225–30, 1986.

Mackie, Ventresca, Fuller and Bye, "Pharmacokinetics of intravenous fluticasone proprionate in healthy volunteers," *Br. J. Clin. Pharmacol.*, 41:539–42, 1996.

Manekar, Puranik and Joshi, "Microencapsulation of propranolol hydrochloride by the solvent evaporation technique," *J. Microencapsul.*, 9(1):63–66, 1992.

McConnell and Howarth, "The airway anti-inflammatory effects of fluticasone propionate," *Rev. Contemp. Pharmacother.*, 9:523–33, 1998.

McCullough and Juliano, "Organ-selective action of an antitumor drug: pharmacologic studies of liposome-encapsulated beta-cytosine arabinoside administered via the respiratory system of the rat," *J. Nat'l Cancer Inst*, 63(3):727–31, 1979.

Meibohm, Möllmann, Wagner, Hochhaus, Möllmann and Derendorf. "The Clinical Pharmacology of Fluticasone Propionate," *Rev. Contemp. Pharmacother.*, 9(8):535–49, 1998.

Meijer, de Lange, Breimer, de Boer, Workel and de Kloet, "Penetration of dexamethasone into brain glucocorticoid targets is enhanced in mdr1A P-glycoprotein knockout mice," *Endocrinology*, 139(4):1789–93, 1998.

Meisner, "Liposomes as a pulmonary drug delivery system," in "Pharmaceutical particulate carriers," Rolland (ed.), Marcel Dekker, New York, pp. 31–63, 1993.

Melchor, Biddiscome, Hak, Short and Spiro, "Lung disposition patterns of directly labeled salbutamol in normal subjects and in patients with reversible airflow obstructions," Thorax, 48:506–11, 1993.

Meyer, J. M., C. L. Wenzel et al., "Salmeterol: a novel, long-acting beta 2-agonist." Ann. Pharmacotherapy, 27(12): 1478–87, 1993.

Miller, Spencer, Pearce, Pisell, Azrieli, Tanapat, Moday, Rhee and McEwen, "Glucocorticoid receptors are differentially expressed in the cells and tissues of the immune system." Cell Immunol., 186(1):45–54, 1998.

Milsap and Jusko, "Binding of prednisolone to al-acid glycoprotein," J. Ster. Biochem., 18(2):191–94, 1983.

Moellmann, Rohdewald, Barth, Verho and Derendorf. "Pharmacokinetics and dose linearity testing of methylprednisolone phosphate." Biopharm. Drug Dispos., 10:453, 1989.

Moellmann, Rohdewald, Schmidt, Salomon and Derendorf, Eur. J. Clin. Pharmacol., 29:85–89, 1985.

Möllmann et al. "Pharmacokinetic and pharmacodynamic evaluation of fluticasone propionate after inhaled administration," Eur. J. Clin. Pharmacol. 53(6):459–67, 1998.

Möllmann et al. "Pharmacokinetic/pharmacodynamic evaluation of systemic effects of flunisolide after inhalation." J. Clin. Pharmacol., 37(10):893–903, 1997.

Möllmann, Hochhaus, Rohatagi, Barth, Derendorf, Krieg, Weisser and Möllmann, "Pharmacokinetics and pharmacodynamics of cloprednol," Int. J. Clin. Pharmacol. Ther., 34(1):1–5, 1996.

Möllmann, Rohdewald, Schmidt and Derendorf, "Pharmacokinetics of triamcinolone acetonide and its phosphate ester," Eur. J. Clin. Pharmacol., 29:85–89, 1985.

Mueller and Renkawitz, "The glucocorticoid receptor," Biochemica et Biophysica Acta, 1088:171–82, 1991.

Munck, Mendel, Smith and Orti, "Glucocorticoid Receptors and Actions," American Reviews of Respiratory Diseases, 141:S2–10, 1990.

Mutschler and Derendorf, in "Drug Actions," CRC Press, Boca Raton, Fla., pp. 286–87, 1995.

Newman, "Aerosol deposition considerations in inhalation therapy," Chest, 82(2 Suppl):152S–60S, 1981.

Newman, S. P., "Aerosol deposition considerations in inhalation therapy" Chest, 82(2 Suppl): 152S–160S, 1985.

Newman, Brown, Steed, Reader and Kladders, "Lung deposition of fenoterol and flunisolide delivered using a novel device for inhaled medicines: comparison of RESPIMAT with conventional metered-dose inhalers with and without spacer devices," Chest, 113(4):957–63, 1998.

Newman, Moren, Pavia, Little and Clarke, "Deposition of pressurized suspension aerosols inhaled through extension devices," Am. Rev. Respir. Dis., 124(3):317–20, 1981.

Newman, Steed, Hooper, Kallen and Borgström. "Comparison of gamma scintigraphy and a pharmacokinetic technique for assessing pulmonary deposition of terbutaline sulphate delivered by pressurized metered dose inhaler," Pharm. Res., 12(2):231–36, 1995.

Newman, Steed, Reader, Hooper and Zierenberg, "Efficient delivery to the lungs of flunisolide aerosol from a new portable hand-held multidose nebulizer," J. Pharm. Sci., 85:960–64, 1997.

Newman, Weisz, Talaee and Clarke, "Improvement of drug delivery with a breath actuated pressurized aerosol for patients with poor inhaler technique," Thorax, 46(10): 716–16, 1991.

Nicklas, National and international guidelines for the diagnosis and treatment of asthmma," Curr. Opin. Pulm. Med. 3(1):51–55, 1997.

Nicolaizik, Marchant, Preece and Warner, "Endocrine and lung function in asthmatic children on inhaled corticosteroids," Am. J. Respir. Crit. Care Med. 150:624–28, 1994.

Nolen, H. r., R. N. Fedorak et al. "Budesonide-beta-D-glucuronide: a potential prodrug for treatment of ulcerative colitis." J. Pharm. Sci., 84(6): 677–81, 1995.

Pakes, Brogden, Heel, Speight and Avery, "Flunisolide: a review of its pharmacological properties and therapeutic efficacy in rhinitis," Drugs, 19(6):397–411, 1980.

Paterson, Woolcock and Shenfield, "Bronchodilator drugs," Am. Rev. Respir. Dis., 120(5):1149–88, 1979.

Pauwels, Newman and Borgström, "Comparison of gamma scintigraphy and a pharmacokinetic technique for assessing pulmonary deposition of terbutaline sulphate delivered by pressurized metered dose inhaler," Pharm. Res., 12(2):231–36, 1995.

Pavord and Knox, "Pharmacokinetic optimization of inhaled steroid therapy in asthma," Clin. Pharmacokinet., 25(2): 126–35, 1993.

Pedersen, "Inhalers and nebulizers: which to choose and why," Respir. Med., 90(2):69–77, 1996.

Peets, Staub and Synchowics, "Plasma protein binding of betamethsone-3H, dexamethasone-3H and cortisol-14C—a comparative study," Biochem. Pharmacol., 18:1655–63, 1969.

Pillai, Yeates, Miller and Hickey, "Controlled dissolution from wax-coated aerosol particles in canine lungs," J. Appl. Physiol., 84(2):717–25, 1998.

Pillai, R. S., D. B. Yeates, et al. "Controlled dissolution from wax-coated aerosol particles in canine lungs." J. Appl. Physiol., 81:1878–1883, 1998.

Pratt, "Glucocorticoid receptor structure and the initial events in signal transduction," Mol End Ster. Horm. Action, 119–32), 1990.

Ralston, Hjelmeland, Klausner, Weinstein and Blumenthal, "Carboxyfluorescein as a probe for liposome-cell interactions effect of impurities, and purification of the dye," Biochim. Biophys. Acta, 649:133–37, 1981.

Reed, "New therapeutic approaches in asthma," J. Allergy Clin. Immunol., 77(4):537–43, 1986.

Reul, van den Bosch and de Kloet, "Relative occupation of type-I and type-II corticosteroid receptors in rat brain following stress and dexamethasone treatment: functional implications." J. Endocr. 115:459–67, 1987.

Rimwood and Homes, in "Liposomes, A Practical Approach." New (ed.), Oxford University Press, New York. pp. 126–27, 1990.

Rocci, D'Ambrosio, Johnson and Jusko, "Prednisolone Binding to Albumin and Transcortin in the Presence of Cortisol." Biochem. Pharmacol., 31(3):289–92, 1982.

Rohatagi, Bye, Falcoz, Mackie, Meibohm, Möllmann and Derendorf, "Dynamic modeling of cortisol reduction after inhaled administration of fluticasone propionate," J. Clin. Pharmacol., 36(10):938–41, 1996.

Rohatagi, Hochhaus, Möllmann, Barth, Galia, Erdmann, Sourgens and Derendorf, "Pharmacokinetic and pharmacodynamic evaluation of triamcinolone acetonide after intravenous, oral, and inhaled administration," J. Clin. Pharmacol, 35(12):1187–93, 1995.

Rohdewald, Möllmann and Hochhaus, "Affinities of glucocorticoids for glucocorticoid receptors in the human lung," *Agents and Action,* 17(3/4):290–91, 1985a.

Rohdewald, Möllmann and Hochhaus, "Receptor binding affinities of commercial glucocorticoids to the glucocorticoid receptor of human lung," *Atemw-Lungenhrkh.,* 10:484–87, 1984.

Rohdewald, Möllmann, Barth, Rehder and Derendorf, "Pharmacokinetics of dexamethasone and its phosphate ester," *Biopharm. Drug Dispo.,* 8(3):205–12, 1987.

Rohdewald, Möllmann, Mueller and Hochhaus, "Glucocorticoid receptors in the respiration tract," Bochumer Treff 1984, Rezeptoren und nervoese Versorgung des bronchopulmonalen Systems, Verlag Gedon & Reuss., Munich, pp. 223–42, 1985b.

Ryrfeldt, Andersson, Edsbaecker, Tonnesson, Davies and Pauwels, "Pharmacokinetics and metabolism of budesonide, a selective glucocorticoid," *Eur. J. Respir. Dis.,* 63(Suppl. 122):86–95, 1982.

Ryrfeldt, Persson and Nilsson, "Pulmonary disposition of the potent glucocorticoid budesonide, evaluated in an isolate perfused rat lung model," *Biochem. Pharmacol.,* 38(1):17–22, 1989.

Schinkel, Wagenaar, van Deemter, Mol and Borst, "Absence of the mdr1a P-Glycoprotein in mice affects tissue distribution and pharmacokinetics of dexamethasone, digoxin, and cyclosporin A," *J. Clin. Invest.,* 96(4):1698–705, 1995.

Schleimer, "Effects of glucocorticosteroids on inflammatory cells relevant to their therapeutic applications in asthma," *Am. Rev. Respir. Dis.,* 141(2 Pt 2):S59–69, 1990.

Schlesinger, "Effects of inhaled acids on respiratory tract defense mechanisms," *Environ. Health Perspect.* 63:25–38, 1985.

Schreier, H., K. I. McNicol et al., "Pulmonary deliver of amikacin liposomes and acute liposome toxicity in sheep." Int. J. Pharm. 87:183–193, 1992.

Schreier, Gonzalez-Rothi and Stecenko, *J. Control Release.* 24:209–23, 1993.

Schreier, Lukyanov, Hochhaus and Gonzalez-Rothi, "Thermodynamic and kinetic aspects of the interaction of triamcinolone acetonide with liposomes." *Proceed. Inter. Symp. Control. Rel. Bioact. Mater.,* 21:228–29, 1994.

Schwiebert, Beck, Stellato, Bickel, Bochner and Schleimer. "Glucocorticosteroid inhibition of cytokine production: relevance to antiallergic actions," *J. Allergy Clin. Immunol.,* 97(1 Pt 2):143–52, 1996.

Selroos and Halme, "Effect of a volumatic spacer and mouth rinsing on systemic absorption of inhaled corticosteroids from a metered dose inhaler and dry power inhaler," *Thorax,* 46(12):891–94, 1991.

Sergeev, Kalinin and Dukhanin, "Plasma membrane of thymocytes—home of specific glucocorticoid binding sites." *Biull. Eksp. Biol. Med.,* 102(8):192–94, 1986.

Shah, Konecny, Everett, McCullough, Noorizadeh and Skelly, "In vitro dissolution profile of water-insoluble drug dosage forms in the presence of surfactants," *Pharm. Res.,* 6(7):612–18, 1989.

Shaw, "Liposomal retention of a modified anti-inflammatory steroid," *Biochem. J.,* 158:473–76, 1976.

Shaw, "Pharmacology of fluticasone propionate," *Respir. Med.,* 88 Suppl. A:5–8, 1994.

Silberstein and David, "The regulation of human eosinophil function by cytokines," *Immunol. Today,* 8:380–85, 1987.

Spencer and McTavish, "Budesonide. A review of its pharmacological properties and therapeutic efficacy in inflammatory asthma," *Drugs,* 50(5):854–72, 1995.

Srichana, Martin and Marriott, "Dry powder inhalers: the influence of device resistance and powder formulation on drug and lactose deposition in vitro," *Eur. J. Pharm. Sci.,* 7(1):73–80, 1998.

Stewart, "Colorimetric determination of phospholipids with ammonium ferrothiocyante," *Anal Chem.,* 104:10–14, 1980.

Suarez, "Biopharmaceutical Aspects Relevant to Pulmonarv Targeting of Inhaled Glucocorticoids: Application to Liposomes and Dry Powders," *PhD Dissertation,* 1997.

Suarez, Gonzalez-Rothi and Hochhaus, "The effect of dose and release rate on pulmonary targeting of glucocorticoids using liposomes as a model dosage form," *Pharm. Res.,* 13(suppl): 157S, 1996.

Suarez Gonzalez-Rothi, Schreier and Hochhaus, "The effect of dose and release rate on pulmonary targeting of liposomal triamcinolone acetonide phosphate," *Pharm. Res.,* 15(3):461–65, 1998.

Suzuki, Nakata, Nagai, Goto, Nishimura and Okutani, "Synthesis of silicon-based polymer films by UV laser ablation deposition of poly(methylphenylsilane)," *Mat. Sci. Eng. A.,* 246:36–44, 1998.

Svedmyr, N. and C. G. Lofdahl, "The use of beta 2-adrenoceptor agonists in the treatment of bronchial asthma." *Pharmacol. Toxicol.,* 78(1):3–11, 1996.

Therin, Christel, Li, Garreau and Vert, "In vivo degradation of massive poly(alpha-hydroxy acids): validation of in vitro findings," *Biomaterials,* 13(9):594–600, 1992.

Thies, "Microcapsules as drug delivery devices," *Crit Rev. Biomed. Eng.,* 8(4):335–83, 1982.

Thorsson, Dahlström, Edsbaecker, Kallen, Paulson and Wiren, "Pharmacokinetics and systemic effects of inhaled fluticasone propionate in healthy subjects," *Br. J. Clin. Pharmacol.,* 43(2): 155–61, 1997.

Thorsson, Edsbacker and Conradson, "Lung deposition of budesonide from Turbuhaler is twice that from a pressurized metered-dose inhaler P-MDI," *Eur. Respir. J.,* 7:1839–44, 1994.

Tremblay, Therien, Rocheleau and Cormier, *Eur. J. Clin. Inv.,* 23:656–61, 1993.

Tunek, Sjodin and Hallstrom, "Reversible formation of fatty acid esters of budesonide, an anti-asthma glucocorticoid, in human lung and liver microsomes," *Drug Metab. Dispos.,* 25(11):1311–17, 1997.

Ventresca, Mackie, Moss, McDowall and Bye, "Absorption of oral fluticasone propionate in healthy subjects," *Am. J. Resp. Crit. Care Med.,* 149:A214, 1994.

Vidgren, Waldrep, Arppe, Black, Rodarte, Cole and Knight, "A study of $^{99m}$technetium-labelled beclomethasone diprorionate dilauroylphosphatidylcholine liposome aerosol in normal volunteers," *Int. J. Pharm.,* 115:209–16, 1995.

Ward, Woodhouse, Mather, Farr, Okikawa, Lloyd, Schuster and Rubsamen, "Morphine pharmacokinetics after pulmonary administration from a novel aerosol delivery system," *Clin. Pharmacol. Ther.,* 62(6):596–609, 1997.

Wichert, B. V., R. J. Gonzalez-Rothi, et al., "Amikacin liposomes: preparation, characterization, and in vitro activity against Mycobacteriurn avium-intracellulare infection in alveolar macrophages." *Int. J. Pharmaceut.,* 78:227–235, 1992.

Witschi and Mrsny, "In vitro evaluation of microparticles and polymer gels for use as nasal platforms for protein delivery [In Process Citation]," *Pharm. Res.,* 16(3):382–90, 1999.

Wolff, Baxter, Kollmann and Lee, "Nature of Steroid-Glucocorticoid Receptor Interactions:

Thermodynamic Analysis of the Binding Reaction," *Biochemisiry*, 17:3201–07, 1978.

Wuerthwein, Rehder and Rohdewald, "Lipophilicity and receptor affinity of glucocorticoids," *Pharm. Ztg. Wiss.*, 137(4):161–67, 1992.

Zeng, Martin and Marriott, "The Controlled Delivery of Drugs to the Lungs," *Int. J. Pharm.*, 124:149–64, 1995.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. A medicament, comprising:
a plurality of coated drug particles, each of said coated drug particles having an average particle size of less than 50 μm in diameter, the surface of said particles comprising at least a first coating layer of biodegradable and bio-compatible material, said coating layer being a continuous and non-porous layer, wherein an average thickness of said coating layer is between 1 and 500 nm, wherein said coating layer is exclusive of said drug provided by said drug particles.

2. The medicament according to claim 1, wherein said coating layer material is at least one selected from the group consisting of PLA, PGA, PLGA and cellulose compounds.

3. The medicament according to claim 1, wherein said plurality of said coated drug particles have an average particle size of less than 20 μm in diameter.

4. The medicament according to claim 1, wherein said coated drug particles have an average particle size of less than 10 μm in diameter.

5. The medicament according to claim 1, wherein said coated drug particles have an average particle size of less than 1 μm in diameter.

6. The medicament according to claim 1, wherein said coated drug particles have an average particle size of less than 0.1 μm.

7. The medicament according to claim 1, wherein the average thickness of said coating layer is between 1 and 400 nm.

8. The medicament according to claim 1, wherein the average thickness of said coating layer is between 3 and 200 nm.

9. The medicament according to claim 1, wherein the average thickness of said coating layer is between 5 and 50 μm.

10. The medicament according to claim 1, wherein the average thickness of said coating layer is between 50 and 500 nm.

11. The medicament according to claim 1, wherein the average thickness of said coating layer is between 150 and 500 nm.

12. The medicament according to claim 1, wherein the average thickness of said coating layer is between 300 and 500 nm.

13. The medicament according to claim 1, wherein the average size of said coated drug particles is less than 50 nm in diameter.

14. The medicament according to claim 1, wherein the average size of said coated drug particles is less than 30 nm in diameter.

15. The medicament according to claim 1, wherein the average size of said coated drug particles is less than 10 nm in diameter.

16. The medicament according to claim 1, wherein the average size of said coated drug particles is less than 5 nm in diameter.

17. The medicament according to claim 1, wherein said coated drug particles comprise at least one drug selected from the group consisting of anti-allergics, antibiotics, anti-inflammatories and bronchodilatory drugs.

18. The medicament according to claim 1, wherein said coated drug particles comprise at least one drug selected from the group consisting of budesonide, triamcinolone acetonide and rifampicin.

19. A pharmaceutical formulation comprising the medicament of claim 1 and a pharmaceutically acceptable solution.

20. The formulation according to claim 19, wherein said formulation has from 0.01% to 10% by weight of said medicament relative to the total weight of said formulation.

21. The formulation according to claim 19 containing from 0.1% to 1% by weight of said medicament relative to the total weight of said formulation.

22. The formulation according to claim 19, wherein about 20% to about 50% by weight of said medicament is a respirable fraction.

23. The formulation according to claim 19, wherein at least 50% by weight of said medicament is a respirable fraction.

24. The formulation according to claim 19, further comprising at least a second medicament.

25. The formulation according to claim 24, wherein said second medicament is a particulate medicament.

26. The formulation according to claim 24, wherein said second medicament comprises a medicament comprising a plurality of coated drug particles, each of said coated drug particles having an average particle size of less than 50 μm in diameter, the surface of said particles comprising at least a first coating layer of biodegradable and bio-compatible material, said coating layer being a continuous and non-porous layer, wherein an average thickness of said coating layer is between 1 and 500 nm, wherein said coating layer is exclusive of said drug provided by said drug particles.

27. The formulation according to claim 19, further comprising a first bronchodilatory medicament and a second medicament, said medicaments each being at least one selected from the group consisting of anti-inflammatory agents, bronchodilatory agents, antibiotic agents and anti-allergic agents.

28. The formulation according to claim 19, further comprising structure for aerosol administration of said formulation.

29. The formulation according to claim 28, wherein said structure for aerosol administration includes a propellant.

30. The formulation according to claim 29, wherein said propellant is at least one selected from the group consisting of fluorocarbons and hydrogen-containing chlorofluoracarbons.

31. A therapeutic kit comprising the medicament of claim 1 and instructions for the administration of said medicament.

32. A therapeutic kit comprising the formulation according to claim 19 and instructions for the administration of said medicament.

33. The therapeutic kit of claim 31, further comprising an aerosol delivery apparatus or a medical device suitable for pulmonary administration of said medicament.

34. The therapeutic kit of claim 32, further comprising an aerosol delivery apparatus or a medical device suitable for pulmonary administration of said medicament.

35. A method for treating patients, comprising the steps of:

providing a medicament comprising a plurality of coated drug particles, each of said coated drug particles having an average particle size of less than 50 μm in diameter, the surface of said particles comprising at least a first coating layer of biodegradable and bio-compatible material, said coating layer being a continuous and non-porous layer, wherein an average thickness of said coating layer is between 1 and 500 nm and wherein said coating layer is exclusive of said drug provided by said drug particles, and treating a respiratory disorder or pulmonary infection in a human patient using said medicament.

36. The method of claim 35, wherein said coated drug particles have an average particle size of less than 20 μm in diameter.

* * * * *